United States Patent
Allen et al.

(10) Patent No.: US 12,161,712 B2
(45) Date of Patent: Dec. 10, 2024

(54) BROADLY REACTIVE IMMUNOGENS OF INFLUENZA H3 VIRUS, COMPOSITIONS AND METHODS OF USE THEREOF

(71) Applicant: University of Georgia Research Foundation, Athens, GA (US)

(72) Inventors: James Daniel Allen, Athens, GA (US); Ted Milburn Ross, Athens, GA (US); Terianne Maiko Wong, Athens, GA (US)

(73) Assignee: University of Georgia Research Foundation, Athens, GA (US)

( * ) Notice: Subject to any disclaimer, the term of this patent is extended or adjusted under 35 U.S.C. 154(b) by 0 days.

(21) Appl. No.: 17/260,045

(22) PCT Filed: Jul. 12, 2019

(86) PCT No.: PCT/US2019/041679
§ 371 (c)(1),
(2) Date: Jan. 13, 2021

(87) PCT Pub. No.: WO2020/014656
PCT Pub. Date: Jan. 16, 2020

(65) Prior Publication Data
US 2021/0379180 A1    Dec. 9, 2021

Related U.S. Application Data

(60) Provisional application No. 62/697,846, filed on Jul. 13, 2018.

(51) Int. Cl.
| | |
|---|---|
| *A61K 39/145* | (2006.01) |
| *C12N 7/00* | (2006.01) |
| *A61K 39/00* | (2006.01) |

(52) U.S. Cl.
CPC .............. *A61K 39/145* (2013.01); *C12N 7/00* (2013.01); *A61K 2039/55505* (2013.01); *A61K 2039/55566* (2013.01); *C12N 2760/16122* (2013.01); *C12N 2760/16123* (2013.01)

(58) Field of Classification Search
None
See application file for complete search history.

(56) References Cited

U.S. PATENT DOCUMENTS

| | | | |
|---|---|---|---|
| 5,662,907 A | 9/1997 | Kubo et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,406,705 B1 | 6/2002 | Davis et al. | |
| 6,429,199 B1 | 8/2002 | Krieg et al. | |
| 2002/0106798 A1 | 8/2002 | Robinson et al. | |
| 2010/0166769 A1 | 7/2010 | Hsiao et al. | |
| 2015/0030628 A1 | 1/2015 | Ross et al. | |
| 2016/0130306 A1* | 5/2016 | Tharakaraman ... | C07K 16/1018 424/139.1 |
| 2017/0049879 A1 | 2/2017 | Vitelli et al. | |
| 2017/0165353 A1 | 6/2017 | Draghia-Akli et al. | |
| 2018/0177862 A1 | 6/2018 | Settembre et al. | |

FOREIGN PATENT DOCUMENTS

| | | |
|---|---|---|
| WO | 2016207853 A2 | 12/2016 |
| WO | 2017053374 A1 | 3/2017 |
| WO | 2018075592 A1 | 4/2018 |
| WO | 2018085488 A1 | 5/2018 |
| WO | 2020014675 A1 | 1/2020 |

OTHER PUBLICATIONS

GenBank Accession AAT12657.1, hemagglutinin [Influenza A virus (A/Denmark/32/2003(H3N2))], 2005.*
GenBank Accession LC090954, Influenza A virus (A/Fukuoka/73-371/2013(H3N2)) viral cRNA, segment 4, complete sequence, 2015.*
GenBank Accession BAT21748, hemagglutinin [Influenza A virus (A/Fukuoka/73-371/2013(H3N2))], 2015.*
GenBank Accession AGL06609, hemagglutinin [Influenza A virus (A/South Carolina/14/2012(H3N2))]., 2017.*
GenBank Accession AFN19429, hemagglutinin [Influenza A virus (A/Singapore/GP1536/2011(H3N2))], 2012.*
GenBank Accession CY124229, Influenza A virus (A/Singapore/GP1536/2011(H3N2)) hemagglutinin (HA) gene, complete cds., 2012.*
GenBank Accession: KC535393, Influenza A virus (A/New York/01/2010(H3N2)) segment 4 hemagglutinin (HA) gene, complete cds, 2017.*
GenBank Accession: CY008051, Influenza A virus (A/Canterbury/29/2005(H3N2)) segment 4, complete sequence, 2006.*
GenBank Accession: ABC67675, Influenza A virus (A/Canterbury/29/2005(H3N2)) segment 4, complete sequence, 2006.*
GenBank Accession: AGF68758, hemagglutinin [Influenza A virus (A/New York/01/2010(H3N2))], 2017.*
International Search Report and Written Opinion issued in corresponding International Patent Application No. PCT/US19/41679, mailed Nov. 6, 2019 (12 pages).

(Continued)

*Primary Examiner* — Benjamin P Blumel
(74) *Attorney, Agent, or Firm* — Greenberg Traurig LLP; Melissa Hunter-Ensor; Leslie Serunian

(57) ABSTRACT

Provided herein are non-naturally occurring, broadly reactive, pan-epitopic antigens derived from H3 influenza virus that are immunogenic and are capable of eliciting a broadly reactive immune response, such as a broadly reactive neutralizing antibody response, against H3 virus following introduction into a subject. Also provided are non-naturally, broadly reactive occurring immunogens, vaccines, virus-like particles (VLPs) and compositions comprising the immunogens and vaccines. Methods of generating an immune response in a subject by administering the immunogens, vaccines, VLPs, or compositions thereof are provided. In particular, the immunogens comprise the hemagglutinin (HA) protein of H3 influenza virus strains.

18 Claims, 11 Drawing Sheets
Specification includes a Sequence Listing.

(56) References Cited

OTHER PUBLICATIONS

Abdel-Ghafar et al., "Update on Avian Influenza A (H5N1) Virus Infection in Humans," The New England Journal of Medicine, Jan. 17, 2008, vol. 358, No. 3, pp. 261-273.
Bright et al., "Adamantane Resistance Among Influenza A Viruses Isolated Early During the 2005-2006 Influenza Season in the United States," JAMA, Feb. 22, 2006, vol. 295, No. 8, pp. 891-894.
Bright et al., "Impact of glycosylation on the immunogenicity of a DNA-based influenza H5 HA vaccine," Virology, 2003, vol. 308, pp. 270-278.
Bright et al., "Incidence of adamantane resistance among influenza A (H3N2) viruses isolated worldwide from 1994 to 2005: a cause for concern," The Lancet, Oct. 1, 2005, vol. 366, 1175-1181.
Cao et al., "Cytokine Gene Transfer in Cancer Therapy," Stem Cells, 1998, vol. 16, Suppl. 1, pp. 251-260.
Deres et al., "In vivo priming of virus-specific cytotoxic T lymphocytes with synthetic lipopeptide vaccine," Nature, Nov. 30, 1989, vol. 342, pp. 561-564.
Ekiert et al., "A Highly Conserved Neutralizing Epitope on Group 2 Influenza A Viruses," Science, Aug. 12, 2011, vol. 333, No. 6044, pp. 843-850.
Garcia-Sastre et al., "Influenza A Virus Lacking the NS1 Gene Replicates in Interferon-Deficient Systems," Virology, 1998, vol. 252, pp. 324-330.
Gillim-Ross et al., "Emerging Respiratory Viruses: Challenges and Vaccine Strategies," Clinical Microbiology Reviews, Oct. 2006, vol. 19, No. 4, pp. 614-636.
Green et al., "C3d enhancement of neutralizing antibodies to measles hemagglutinin," Vaccine, 2002, vol. 20, pp. 242-248.
Horimoto et al., "Pandemic Threat Posed by Avian Influenza A Viruses," Clinical Microbiology Reviews, Jan. 2001, vol. 14, No. 1, pp. 129-149.
Kimmel, Alan R., "[54] Identification and characterization of specific clones: Strategy for confirming the validity of presumptive clones," Methods in Enzymology, 1987, vol. 152, pp. 507-511.
Klucker et al., "AF03, An Alternative Squalene Emulsion-Based Vaccine Adjuvant Prepared by a Phase Inversion Temperature Method," Journal of Pharmaceutical Sciences, Dec. 2012, vol. 101, No. 12, pp. 4490-4500.
Krug et al., "Expression and Replication of the Influenza Virus Genome," The Influenza Viruses, 1989, Chapter 2, pp. 89-152.
Kuiper et al., "B7.1 and Cytokines. Synergy in Cancer Gene Therapy," Advances in Experimental Medicine and Biology, 2000, vol. 465, pp. 381-390.
Lotze et al., "Interleukin-2: developing additional cytokine gene therapies using fibroblasts or dendritic cells to enhance tumor immunity," The Cancer Journal from Scientific American, Feb. 2000, vol. 6, Suppl. 1, pp. S61-S66.
Marsh et al., "Highly Conserved Regions of Influenza A Virus Polymerase Gene Segments Are Critical for Efficient Viral RNA Packaging," Journal of Virology, Mar. 2008, vol. 82, No. 5, pp. 2295-2304.
Mitchell et al., "Induction of heterosubtypic immunity to influenza A virus using a DNA vaccine expressing hemagglutinin-C3d fusion proteins," Vaccine, 2003, vol. 21, Nos. 9-10, pp. 902-914.
Pinto et al., "Influenza virus M2 protein has ion channel activity," Cell, May 1, 1992, vol. 69, pp. 517-528.
Richardson et al., "NS2 protein of influenza virus is found in purified virus and phosphorylated in infected cells," Archives of Virology, 1991, vol. 116, pp. 69-80.
Ross et al., "C3d enhancement of antibodies to hemagglutinin accelerates protection against influenza virus challenge," Nature Immunology, Aug. 2000, vol. 1, No. 2, pp. 127-131.
Salgaller et al., "Use of Cellular and Cytokine Adjuvants in the Immunotherapy of Cancer," Journal of Surgical Oncology, 1998, vol. 68, pp. 122-138.
Tharakaraman et al., "Broadly Neutralizing Influenza Hemagglutinin Stem-Specific Antibody CR8020 Targets Residues that Are Prone to Escape due to Host Selection Pressure," Cell Host & Microbe, May 14, 2014, vol. 15, pp. 644-651.
Wahl et al., "[43] Molecular hybridization of immobilized nucleic acids: Theoretical concepts and practical considerations," Methods in Enzymology, 1987, vol. 152, pp. 399-407.
Ward et al., "Expression and analysis of the NS2 protein of influenza A virus," Archives of Virology, 1995, vol. 140, pp. 2067-2073.
Yasuda et al., "Molecular Assembly of Influenza Virus: Association of the NS2 Protein with Virion Matrix," Virology, 1993, vol. 196, pp. 249-255.
Zebedee et al., "Influenza A Virus M2 Protein: Monoclonal Antibody Restriction of Virus Growth and Detection of M2 in Virions," Journal of Virology, Aug. 1988, vol. 62, No. 8, pp. 2762-2772.
Extended European Search Report dated May 17, 2022 in corresponding European Patent Application No. 19833422.9 (9 pages).
Office Action dated Aug. 7, 2023 in corresponding Canadian Patent Application No. 3,106,400 (6 pages).
GenBank Accession No. AAZ38506.1 (2 pages).
GenBank Accession No. ABC67675.1 (2 pages).
GenBank Accession No. AGF68758.1 (2 pages).
Office Action dated Dec. 28, 2023 in corresponding Chinese Patent Application No. 201980060011.X (9 pages).
English translation of Office Action dated Dec. 28, 2023 in corresponding Chinese Patent Application No. 201980060011.X (7 pages).

\* cited by examiner

FIG. 1A

TJ-1 HA
MKTIIALSYILCLVFAQKLPGNDNSTATLCLGHHAVPNGTIVKTITNDQIEVTNATELVQSS
STGGICDSPHQILDGENCTLIDALLGDPQCDGFQNKKWDLFVERSKAYSNCYPYDVPD
YASLRSLVASSGTLEFNNESFNWTGVTQNGTSSACKRRSNKSFFSRLNWLTHLKYKYP
ALNVTMPNNEKFDKLYIWGVHHPGTDSDQISLYAQASGRITVSTKRSQQTVIPNIGSRP
RVRDVSSRISIYWTIVKPGDILLINSTGNLIAPRGYFKIRSGKSSIMRSDAPIGKCNSECITP
NGSIPNDKPFQNVNRITYGACPRYVKQNTLKLATGMRNVPEKQTRGIFGAIAGFIENGW
EGMVDGWYGFRHQNSEGIGQAADLKSTQAAINQINGKLNRLIGKTNEKFHQIEKEFSEV
EGRIQDLEKYVEDTKIDLWSYNAELLVALENQHTIDLTDSEMNKLFERTKKQLRENAED
MGNGCFKIYHKCDNACIGSIRNGTYDHDVYRDEALNNRFQIKGVELKSGYKDWILWISF
AISCFLLCVALLGFIMWACQKGNIRCNICI
(SEQ ID NO: 3)

TJ-2 HA
MKTIIALSYILCLVFAQKLPGNDNSTATLCLGHHAVPNGTIVKTITNDQIEVTNATELVQSS
STGGICDSPHQILDGENCTLIDALLGDPQCDGFQNKKWDLFVERSKAYSNCYPYDVPD
YASLRSLVASSGTLEFNNESFNWTGVTQNGTSSACKRRSNNSFFSRLNWLTHLKFKYP
ALNVTMPNNEKFDKLYIWGVHHPGTDNDQISLYAQASGRITVSTKRSQQTVIPNIGSRP
RVRDIPSRISIYWTIVKPGDILLINSTGNLIAPRGYFKIRSGKSSIMRSDAPIGKCNSECITP
NGSIPNDKPFQNVNRITYGACPRYVKQNTLKLATGMRNVPEKQTRGIFGAIAGFIENGW
EGMVDGWYGFRHQNSEGIGQAADLKSTQAAINQINGKLNRLIGKTNEKFHQIEKEFSEV
EGRIQDLEKYVEDTKIDLWSYNAELLVALENQHTIDLTDSEMNKLFERTKKQLRENAED
MGNGCFKIYHKCDNACIGSIRNGTYDHDVYRDEALNNRFQIKGVELKSGYKDWILWISF
AISCFLLCVALLGFIMWACQKGNIRCNICI
(SEQ ID NO: 4)

TJ-3 HA
MKTIIALSYILCLVFAQKLPGNDNSTATLCLGHHAVPNGTIVKTITNDQIEVTNATELVQSS
STGGICDSPHQILDGENCTLIDALLGDPQCDGFQNKKWDLFVERSKAYSNCYPYDVPD
YASLRSLVASSGTLEFNNESFNWTGVTQNGTSSACKRRSNNSFFSRLNWLTHLKFKYP
ALNVTMPNNEKFDKLYIWGVHHPGTDNDQIFLYAQASGRITVSTKRSQQTVIPNIGSRP
RVRNIPSRISIYWTIVKPGDILLINSTGNLIAPRGYFKIRSGKSSIMRSDAPIGKCNSECITP
NGSIPNDKPFQNVNRITYGACPRYVKQNTLKLATGMRNVPEKQTRGIFGAIAGFIENGW
EGMVDGWYGFRHQNSEGIGQAADLKSTQAAINQINGKLNRLIGKTNEKFHQIEKEFSEV
EGRIQDLEKYVEDTKIDLWSYNAELLVALENQHTIDLTDSEMNKLFERTKKQLRENAED
MGNGCFKIYHKCDNACIGSIRNGTYDHDVYRDEALNNRFQIKGVELKSGYKDWILWISF
AISCFLLCVALLGFIMWACQKGNIRCNICI
(SEQ ID NO: 5)

FIG. 1B

TJ-4 HA
MKTIIALSYILCLVFAQKLPGNDNSTATLCLGHHAVPNGTIVKTITNDQIEVTNATELVQSS
STGGICDSPHQILDGENCTLIDALLGDPQCDGFQNKKWDLFVERSKAYSNCYPYDVPD
YASLRSLVASSGTLEFNNESFNWTGVTQNGTSSACKRRSNKSFFSRLNWLTHLKFKYP
ALNVTMPNNEKFDKLYIWGVHHPGTDNDQISLYAQASGRITVSTKRSQQTVIPNIGSRP
RVRDVPSRISIYWTIVKPGDILLINSTGNLIAPRGYFKIRSGKSSIMRSDAPIGKCNSECITP
NGSIPNDKPFQNVNRITYGACPRYVKQNTLKLATGMRNVPEKQTRGIFGAIAGFIENGW
EGMVDGWYGFRHQNSEGIGQAADLKSTQAAINQINGKLNRLIGKTNEKFHQIEKEFSEV
EGRIQDLEKYVEDTKIDLWSYNAELLVALENQHTIDLTDSEMNKLFERTKKQLRENAED
MGNGCFKIYHKCDNACIGSIRNGTYDHDVYRDEALNNRFQIKGVELKSGYKDWILWISF
AISCFLLCVALLGFIMWACQKGNIRCNICI
(SEQ ID NO: 6)

TJ-5 HA (1-566AA)
MKTIIALSYILCLVFAQKLPGNDNSTATLCLGHHAVPNGTIVKTITNDQIEVTNATELVQSS
STGEICDSPHQILDGENCTLIDALLGDPQCDGFQNKKWDLFVERSKAYSNCYPYDVPDY
ASLRSLVASSGTLEFNNESFNWTGVTQNGTSSACIRRSNNSFFSRLNWLTHLNFKYPAL
NVTMPNNEQFDKLYIWGVHHPGTDKDQIFLYAQASGRITVSTKRSQQAVIPNIGSRPRV
RNIPSRISIYWTIVKPGDILLINSTGNLIAPRGYFKIRSGKSSIMRSDAPIGKCNSECITPNG
SIPNDKPFQNVNRITYGACPRYVKQSTLKLATGMRNVPEKQTRGIFGAIAGFIENGWEG
MVDGWYGFRHQNSEGRGQAADLKSTQAAIDQINGKLNRLIGKTNEKFHQIEKEFSEVE
GRIQDLEKYVEDTKIDLWSYNAELLVALENQHTIDLTDSEMNKLFEKTKKQLRENAEDM
GNGCFKIYHKCDNACIGSIRNGTYDHDVYRDEALNNRFQIKGVELKSGYKDWILWISFAI
SCFLLCVALLGFIMWACQKGNIRCNICI
(SEQ ID NO: 7)

TJ-6 HA (1-566AA)
MKTIIALSYILCLVFAQKLPGNDNSTATLCLGHHAVPNGTIVKTITNDQIEVTNATELVQNS
SIGEICDSPHQILDGENCTLIDALLGDPQCDGFQNKKWDLFVERSKAYSNCYPYDVPDY
ASLRSLVASSGTLEFNNESFNWTGVTQNGTSSACIRRSNSSFFSRLNWLTHLNFKYPAL
NVTMPNNEQFDKLYIWGVHHPGTDKDQIFLYAQSSGRITVSTKRSQQAVIPNIGSRPRIR
NIPSRISIYWTIVKPGDILLINSTGNLIAPRGYFKIRSGKSSIMRSDAPIGKCNSECITPNGSI
PNDKPFQNVNRITYGACPRYVKQSTLKLATGMRNVPEKQTRGIFGAIAGFIENGWEGM
VDGWYGFRHQNSEGRGQAADLKSTQAAIDQINGKLNRLIGKTNEKFHQIEKEFSEVEG
RIQDLEKYVEDTKIDLWSYNAELLVALENQHTIDLTDSEMNKLFEKTKKQLRENAEDMG
NGCFKIYHKCDNACIGSIRNGTYDHDVYRDEALNNRFQIKGVELKSGYKDWILWISFAIS
CFLLCVALLGFIMWACQKGNIRCNICI
(SEQ ID NO: 8)

FIG. 1C

TJ-7 HA (1-566AA)
MKTIIALSYILCLVFAQKLPGNDNSTATLCLGHHAVPNGTIVKTITNDQIEVTNATELVQNS
SIGEICDSPHQILDGENCTLIDALLGDPQCDGFQNKKWDLFVERSKAYSNCYPYDVPDY
ASLRSLVASSGTLEFNNESFNWTGVTQNGTSSACIRRSNSSFFSRLNWLTHLNFKYPAL
NVTMPNNEQFDKLYIWGVHHPGTDKDQIFLYAQSSGRITVSTKRSQQAVIPNIGSRPRIR
NIPSRISIYWTIVKPGDILLINSTGNLIAPRGYFKIRSGKSSIMRSDAPIGKCKSECITPNGSI
PNDKPFQNVNRITYGACPRYVKQSTLKLATGMRNVPEKQTRGIFGAIAGFIENGWEGM
VDGWYGFRHQNSEGRGQAADLKSTQAAIDQINGKLNRLIGKTNEKFHQIEKEFSEVEG
RIQDLEKYVEDTKIDLWSYNAELLVALENQHTIDLTDSEMNKLFEKTKKQLRENAEDMG
NGCFKIYHKCDNACIGSIRNGTYDHDVYRDEALNNRFQIKGVELKSGYKDWILWISFAIS
CFLLCVALLGFIMWACQKGNIRCNICI
(SEQ ID NO: 9)

TJ-8 HA (1-566AA)
MKTIIALSYILCLVFAQKLPGNDNSTATLCLGHHAVPNGTIVKTITNDQIEVTNATELVQSS
STGEICDSPHQILDGKNCTLIDALLGDPQCDGFQNKKWDLFVERSKAYSNCYPYDVPDY
ASLRSLVASSGTLEFNNESFNWTGVTQNGTSSACIRRSNNSFFSRLNWLTHLNFKYPAL
NVTMPNNEQFDKLYIWGVHHPGTDKDQIFLYAQASGRITVSTKRSQQTVIPNIGSRPRV
RNIPSRISIYWTIVKPGDILLINSTGNLIAPRGYFKIRSGKSSIMRSDAPIGKCNSECITPNG
SIPNDKPFQNVNRITYGACPRYVKQSTLKLATGMRNVPEKQTRGIFGAIAGFIENGWEG
MVDGWYGFRHQNSEGRGQAADLKSTQAAIDQINGKLNRLIGKTNEKFHQIEKEFSEVE
GRIQDLEKYVEDTKIDLWSYNAELLVALENQHTIDLTDSEMNKLFEKTKKQLRENAEDM
GNGCFKIYHKCDNACIGSIRNGTYDHDVYRDEALNNRFQIKGVELKSGYKDWILWISFAI
SCFLLCVALLGFIMWACQKGNIRCNICI
(SEQ ID NO: 10)

T-J9 HA (1-566AA)
MKTIIALSYILCLVFAQKLPGNDNSTATLCLGHHAVPNGTIVKTITNDQIEVTNATELVQSS
STGEICDSPHQILDGENCTLIDALLGDPQCDGFQNKKWDLFVERSKAYSNCYPYDVPDY
ASLRSLVASSGTLEFNNESFNWTGVTQNGTSSACIRRSNNSFFSRLNWLTHLNFKYPAL
NVTMPNNEQFDKLYIWGVHHPGTDKDQIFLYAQSSGRITVSTKRSQQAVIPNIGSRPRIR
NIPSRISIYWTIVKPGDILLINSTGNLIAPRGYFKIRSGKSSIMRSDAPIGKCNSECITPNGSI
PNDKPFQNVNRITYGACPRYVKQSTLKLATGMRNVPEKQTRGIFGAIAGFIENGWEGM
VDGWYGFRHQNSEGRGQAADLKSTQAAIDQINGKLNRLIGKTNEKFHQIEKEFSEVEG
RIQDLEKYVEDTKIDLWSYNAELLVALENQHTIDLTDSEMNKLFEKTKKQLRENAEDMG
NGCFKIYHKCDNACIGSIRNGTYDHDVYRDEALNNRFQIKGVELKSGYKDWILWISFAIS
CFLLCVALLGFIMWACQKGNIRCNICI
(SEQ ID NO: 11)

BROADLY REACTIVE IMMUNOGENS OF INFLUENZA H3 VIRUS, COMPOSITIONS AND METHODS OF USE THEREOF

CROSS-REFERENCE TO RELATED APPLICATION

This application is the U.S. national phase application pursuant to 35 U.S.C. § 371 of PCT International Application No.: PCT/US2019/041679, filed Jul. 12, 2019, designating the United States and published in English, which claims priority to and benefit of U.S. Provisional Application No. 62/697,846, filed on Jul. 13, 2018, the entire contents of which are incorporated by reference herein in their entirety.

SEQUENCE LISTING This application contains a Sequence Listing which has been submitted electronically in ASCII format and is hereby incorporated by reference in its entirety. Said ASCII copy, created on Aug. 6, 2019, is named 173093_010501_PCT_SL.txt and is 51,524 bytes in size.

BACKGROUND

In 2017, the U.S. Centers for Disease Control and Prevention estimated that the seasonal flu vaccine was only 42% effective. This limited effectiveness was due to a mutation that occurred in the influenza A (H3N2) vaccine strain that causes flu in infected individuals. In addition, cases of flu caused by influenza B viruses have risen in the 2017 to 2018 time period. Given that a bad flu season can kill on the order of 50,000 people in the United States alone, improved immunogens and vaccines that could provide broad protection against viruses, particularly, against influenza A H3 or H3N2 viruses in present and future circulation, are urgently needed.

SUMMARY OF THE DISCLOSURE

As described below, non-naturally occurring, broadly reactive antigens and antigen sequences derived from the Influenza H3 virus (also referred to as "H3 influenza," "H3 influenza virus," or "H3 virus," herein), such as subtype H3N2, are provided. These H3 virus antigens are typically structural proteins or peptides and include, for example, the hemagglutinin (HA) protein, or the HA1 (head) or HA2 (tail or stalk) portions of the HA protein, and are potent immunogens that elicit a broadly reactive immune response against H3 HA protein and, ultimately, against present and future H3 virus strains in a subject. As referred to herein, the H3 virus antigens or antigen sequences that elicit an immune response in a subject are immunogenic antigens or immunogens. These H3 immunogens are termed broadly reactive and pan-epitopic, because they can elicit the production of broadly reactive antibodies that are directed against different subtypes or strains of H3 viruses having both sequence similarity and variability, and a diversity of epitopes (antigenic determinants) in their antigens and sequences thereof, particularly, the HA antigen.

In an aspect, the non-naturally occurring H3 virus antigen amino acid sequences and the antigens (e.g., structural antigens) comprising the sequences described herein contain broadly reactive epitopes that reflect sequence similarities and variabilities of past, present and future H3 antigens. Such antigen sequences and the antigens comprising the sequences are thus called "non-naturally occurring, broadly reactive, pan-epitopic" antigens. The antigens are immunogenic and, when introduced into or administered to a subject, elicit broadly reactive antibodies, such as neutralizing antibodies, against the H3 virus, in particular, H3 antigens, such as HA, or an antibody binding portion thereof, in the subject. In an embodiment, such H3 antigen sequences are amino acid sequences. In an embodiment, the H3 antigen sequences are polynucleotide sequences, for example, polynucleotide sequences that encode the amino acid sequences of the antigens described herein. For ease of reference, a "non-naturally occurring, broadly reactive, pan-epitopic" antigen of H3 virus described herein is referred to as a "broadly reactive antigen."

The broadly reactive H3 antigens described herein are immunogens as they elicit a broadly reactive immune response in a subject. The immune response is particularly in the form of a neutralizing antibody response, for example, neutralizing antibodies that are specifically directed against the HA antigen of the H3 virus and that neutralize the activity of the HA protein. Accordingly, also provided are immunogens and immunogenic compositions that contain the broadly reactive H3 antigens described herein, including immunogenic compositions, such as vaccines (e.g., polypeptide or polynucleotide products), that induce an immune response directed against H3 virus, such as against the HA protein of H3 virus, in a subject. For ease of reference, a "non-naturally occurring, broadly reactive, pan-epitopic" H3 virus immunogen described herein will be referred to as a "broadly reactive immunogen."

Also provided are methods of using the immunogens as described herein to induce an immune response against H3 influenza infection, disease, and/or the symptoms thereof in a subject. In a particular embodiment, the H3 virus antigen is the HA, HA1, or HA2 protein of H3 influenza virus, or the H3N2 subtype of influenza virus, or a virus type related thereto, or an antibody binding portion thereof. Methods of using the immunogens to induce an immune response in a subject are also provided.

In an aspect, the H3 HA immunogenic antigen has an amino acid sequence that is at least or equal to 85%, at least or equal to 90%, at least or equal to 91%, at least or equal to 92%, at least or equal to 93%, at least or equal to 94%, at least or equal to 95%, at least or equal to 96%, at least or equal to 97%, at least or equal to 98%, or at least or equal to 99% identical to an H3 HA polypeptide (or an HA1 or HA2 polypeptide) sequence of one or more of the HA proteins (called "TJ1-9 HA" herein) as set forth in FIGS. 1A and 1B.

In an aspect, a broadly reactive H3 antigen sequence that is capable of generating an immune response against present and future H3 influenza virus strains may be generated by a method such as described in co-pending provisional patent application No. 62/697,803, filed on Jul. 13, 2018, the contents of which are incorporated herein by reference, and which involves a consideration of the parameters of H3 antigen sequences, e.g., HA antigen sequences, from a time span or range (e.g., a linear time range), such as one or more flu seasons, and geographical location(s) in which the H3 virus was isolated, such as, for example, the Southern or Northern Hemisphere.

Provided in an aspect is a non-naturally occurring, broadly reactive, pan-epitopic antigen of H3 influenza virus (H3 virus) capable of generating an immune response against present and future H3 virus strains; wherein the H3 virus antigen comprises an amino acid sequence that is at least 95% identical to an amino acid sequence of an HA antigen (TJ-1-TJ-9) as set forth in FIGS. 1A-1C.

Provided in another aspect is a non-naturally occurring, broadly reactive, pan-epitopic antigen of H3 influenza virus (H3 virus) capable of generating an immune response against present and future H3 virus strains. In an embodiment, the antigen is hemagglutinin (HA), HA1, or HA2, or an antibody binding portion thereof. In an embodiment, the H3 virus antigen comprises an amino acid sequence that is at least 95% identical or at least 98% identical to an amino acid sequence of an HA antigen as set forth in FIGS. 1A-1C. In a particular embodiment, the H3 virus antigen comprises an amino acid sequence of an HA antigen as set forth in FIGS. 1A-1C.

It will be understood a non-naturally occurring, broadly reactive, pan-epitopic immunogen is provided, which may be referred to interchangeably herein, as a "non-naturally occurring immunogen," a "broadly reactive immunogen," or a "pan-epitopic immunogen," for simplicity.

Provided in another aspect is a virus-like particle (VLP) comprising the H3 virus immunogenic antigen according to the foregoing aspects. In an embodiment, the VLP comprises a polynucleotide encoding the H3 virus antigen.

Provided in another aspect is a non-naturally occurring, pan-epitopic immunogen capable of generating an immune response against present and future H3 influenza (H3) virus strains; wherein the immunogen comprises an amino acid sequence that is at least 95% identical to an amino acid sequence of an HA antigen (TJ-1-TJ-9) as set forth in FIGS. 1A-1C.

Provided in another aspect is a non-naturally occurring, broadly reactive, pan-epitopic immunogen capable of generating an immune response against present and future H3 influenza virus strains. In an embodiment, the H3 virus antigen, immunogen, or VLP elicits the production of neutralizing antibodies. In an embodiment, the antibodies have hemagglutinin inhibitory activity. In an embodiment, the H3 virus antigen, immunogen, or VLP elicits the production of T-lymphocytes.

Provided in another aspect is a pharmaceutically acceptable composition comprising the H3 virus antigen, immunogen, or VLP of any of the foregoing aspects and delineated embodiments, and a pharmaceutically acceptable carrier, diluent, or excipient. In an embodiment, the composition further comprises an adjuvant.

Provided in another aspect is a vaccine or an immunogenic composition comprising the H3 virus antigen, immunogen, or VLP of any of the foregoing aspects and delineated embodiments.

Provided in another aspect is a method of generating an immune response in a subject, in which the method comprises administering to the subject an effective amount of the immunogen, pharmaceutical composition, vaccine, or VLP of any of the foregoing aspects and delineated embodiments. In an embodiment, the immune response elicited comprises the production of neutralizing antibodies and/or T-lymphocytes.

In an aspect, the broadly reactive H3 immunogen is isolated and/or purified. In another aspect, the broadly reactive H3 immunogen is formulated for administration to a subject in need thereof. In another aspect, the broadly reactive H3 immunogen or a composition containing the immunogen is administered to a subject in need thereof in an effective amount to elicit an immune response in the subject. In an embodiment, the immune response elicits neutralizing antibodies. In an embodiment, the immune response is prophylactic or therapeutic.

In another aspect, a vaccine or an immunogenic composition comprising the broadly reactive H3 immunogen is provided.

In another aspect, virus-like particles (VPLs) comprising the broadly reactive H3 immunogen or a sequence thereof are provided. In an embodiment, the sequence is an amino acid sequence. In an embodiment, the sequence is a polynucleotide sequence which encodes the amino acid sequence.

In another aspect, a method of generating an immune response in a subject is provided, in which the method comprises administering to the subject an effective amount of the H3 broadly reactive immunogen, vaccine, VLP, or composition of any of the above aspects and delineated embodiments. In an embodiment of the method, an adjuvant is concomitantly administered to the subject.

Definitions

Unless defined otherwise, all technical and scientific terms used herein have the meaning commonly understood by a person skilled in the art to which this invention pertains or relates. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); Benjamin Lewin, *Genes I'*, published by Oxford University Press, 1994 (ISBN 0-19-854287-9); Kendrew et al. (eds.); *The Encyclopedia of Molecular Biology*, published by Blackwell Science Ltd., 1994 (ISBN 0-632-02182-9); *Molecular Biology and Biotechnology: a Comprehensive Desk Reference*, Robert A. Meyers (ed.), published by VCH Publishers, Inc., 1995 (ISBN 1-56081-569-8); and Hale & Marham, *The Harper Collins Dictionary of Biology* (1991). As used herein, the following terms have the meanings ascribed to them below, unless specified otherwise.

By "adjuvant" is meant a substance or vehicle that non-specifically enhances the immune response to an antigen. Adjuvants may include a suspension of minerals (e.g., alum, aluminum hydroxide, or phosphate) on which antigen is adsorbed; or water-in-oil emulsion in which antigen solution is emulsified in mineral oil (e.g., Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (see, e.g., U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include, without limitation, interleukin-1 (IL-2), the protein memory T-cell attractant "Regulated on Activation, Normal T Expressed and Secreted" (RANTES), granulocyte-macrophage-colony stimulating factor (GM-CSF), tumor necrosis factor-alpha (TNF-α), interferon-gamma (IFN-γ), granulocyte-colony stimulation factor (G-CSF), lymphocyte function-associated antigen 3 (LFA-3, also called CD58), cluster of differentiation antigen 72 (CD72), (a negative regulator of B cell responsiveness), peripheral membrane protein, B7-1 (B7-1, also called CD80), peripheral membrane protein, B7-2 (B7-2, also called CD86), the TNF ligand superfamily member 4 ligand (OX40L) or the type 2 transmembrane glycoprotein receptor belonging to the TNF superfamily (4-1BBL)

By "administer" is meant giving, supplying, dispensing a composition, agent, therapeutic and the like to a subject, or applying or bringing the composition and the like into contact with the subject. Administering or administration may be accomplished by any of a number of routes, such as, for example, without limitation, topical, oral, subcutaneous, intramuscular, intraperitoneal, intravenous (IV), (injection), intrathecal, intramuscular, dermal, intradermal, intracranial, inhalation, rectal, intravaginal, or intraocular.

By "agent" is meant any small molecule chemical compound, antibody, nucleic acid molecule, peptide, polypeptide, or fragments thereof.

By "alteration" is meant a change (increase or decrease) in the expression levels or activity of a gene or polypeptide as detected by standard art known methods such as those described herein. As used herein, an alteration includes a 5% change in expression levels, a 10% change in expression levels, preferably a 25% change, more preferably a 40% change, and most preferably a 50% or greater change in expression levels."

By "ameliorate" is meant decrease, reduce, diminish, suppress, attenuate, arrest, or stabilize the development or progression of a disease or pathological condition.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "antibody" is meant an immunoglobulin (Ig) molecule produced by B lymphoid cells and having a specific amino acid sequence. Antibodies are evoked or elicited in subjects (humans or other animals or mammals) following exposure to a specific antigen (immunogen). A subject capable of generating antibodies/immunoglobulin (i.e., an immune response) directed against a specific antigen/immunogen is said to be immunocompetent. Antibodies are characterized by reacting specifically with (e.g., binding to) an antigen or immunogen in some demonstrable way, antibody and antigen/immunogen each being defined in terms of the other.

"Eliciting an antibody response" refers to the ability of an antigen, immunogen or other molecule to induce the production of antibodies. Antibodies are of different classes, e.g., IgM, IgG, IgA, IgE, IgD and subtypes or subclasses, e.g., IgG1, IgG2, IgG2a, IgG2b, IgG3, IgG4. An antibody/immunoglobulin response elicited in a subject can neutralize a pathogenic (e.g., infectious or disease-causing) agent by binding to epitopes (antigenic determinants) on the agent and blocking or inhibiting the activity of the agent, and/or by forming a binding complex with the agent that is cleared from the system of the subject, e.g., via the liver.

As used herein, "broadly reactive" means that an immune response is elicited against a viral protein (e.g., a virus antigen, antigen sequence, protein, or protein sequence) in a subject that is sufficient to block, inhibit, impede, neutralize, or prevent infection of a broad range of related influenza viruses (such as most or all influenza viruses within a specific subtype, e.g., viruses related to H3 influenza virus).

By "antigen" is meant a compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In some embodiments of the disclosed compositions and methods, the antigen is an influenza hemagglutinin (HA) protein. In many cases, an antigen that elicits or stimulates an immune response in a subject is termed an "immunogen."

The term "antigenic drift" refers to a mechanism for variation in organisms or microorganisms such as viruses that involves the accumulation of mutations within the genes that code for antibody-binding sites (also called antigenic determinants or epitopes). This process results in a new strain of virus/virus particles that is not inhibited or blocked as effectively by antibodies that were originally generated against the antigens of virus strains prior to mutation, thus allowing the virus to spread more easily throughout a partially immune population. By way of example, antigenic drift occurs in both influenza A and influenza B viruses.

In the context of a live virus, the term "attenuated" reflects a virus that is attenuated if its ability to infect a cell or subject and/or its ability to produce disease is reduced (for example, diminished, abrogated, or eliminated) compared to the ability of a wild-type virus to produce disease in the subject. Typically, an attenuated virus retains at least some capacity to elicit an immune response following administration to an immunocompetent subject. In some cases, an attenuated virus is capable of eliciting a protective immune response without causing any signs or symptoms of infection. In some embodiments, the ability of an attenuated virus to cause disease or pathology in a subject is reduced at least about or equal to 5%, or at least about or equal to 10%, or at least about or equal to 25%, at least about or equal to 50%, at least about or equal to 75%, or at least about or equal to 80%, or at least about or equal to 85%, or at least about or equal to 90%, or at least about or equal to 95%, or greater, relative to the ability of a wild-type virus to cause disease or pathology in the subject.

The term "clade" refers to the different categorizations (often called subtypes) of the known influenza viruses, such as, e.g., the influenza A H3N2 virus. Viruses in an H3N2 clade are genetically related, but do not share the exact viral genome. As appreciated by the skilled practitioner, there are many clades and subclades of H3N2 virus subtypes designated in the art. By way of example, one clade is 3C.2a; subclades of this clade include 3C.2a.1, 3C.2a.2, 3C.2a.3 and 3C.2a.4. In addition, there are at least ten different clades of H5N1 virus subtypes designated in the art: clade 0 clade 1, clade 2, clade 3, clade 4, clade 5, clade 6, clade 7, clade 8 and clade 9 (Abdel-Ghafar et al., *N Engl J Med* 358:261-273, 2008). Clade 2 is further divided into subclades (including clade 2.1, clade 2.2, clade 2.3, clade 2.4 and clade 2.5).

A "codon-optimized" nucleic acid (polynucleotide) refers to a nucleic acid sequence that has been altered such that the codons are optimal for expression in a particular system (such as a particular species of group of species). For example, a nucleic acid sequence can be optimized for expression in mammalian cells. Codon optimization does not alter the amino acid sequence of the encoded protein.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of an analyte, compound, agent, or substance to be detected. By "detectable label" is meant a composition that, when linked to a molecule of interest, renders the latter detectable, e.g., via spectroscopic, photochemical, biochemical, immunochemical, or chemical means.

Nonlimiting examples of useful detectable labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition, disorder, or pathology that damages or interferes with the normal function of a cell, tissue, or organ. Examples of diseases include those caused by H3 virus infection and the symptoms and adverse effects that are caused by infection of the body with the H3 virus. Influenza virus causes flu and its symptoms in infected individuals.

By "effective amount" is meant the amount of an active therapeutic agent, composition, compound, biologic (e.g., a vaccine or therapeutic peptide, polypeptide, or polynucleotide) required to ameliorate, reduce, improve, abrogate, diminish, or eliminate the symptoms and/or effects of a disease, condition, or pathology relative to an untreated patient. The effective amount of an immunogen or a composition comprising an immunogen, as used to practice the methods of therapeutic treatment of disease, condition, or pathology caused by the H3 virus, varies depending upon the manner of administration, the age, body weight, and general health of the subject. Ultimately, the attending physician or veterinarian will decide the appropriate amount and dosage regimen. Such amount is referred to as an "effective" amount.

A "therapeutically effective amount" refers to a quantity of a specified agent sufficient to achieve a desired effect in a subject being treated with that agent. For example, this may be the amount of an H3 influenza virus immunogen or vaccine useful for eliciting an immune response in a subject and/or for preventing infection by H3 influenza virus. Ideally, in the context of the present disclosure, a therapeutically effective amount of an influenza vaccine or an anti-influenza immunogenic composition is an amount sufficient to increase resistance to, prevent, ameliorate, reduce, and/or treat infection caused by influenza virus in a subject without causing a substantial cytotoxic effect in the subject. The effective amount of an influenza vaccine of immunogenic composition useful for increasing resistance to, preventing, ameliorating, reducing, and/or treating infection in a subject depends on, for example, the subject being treated, the manner of administration of the therapeutic composition and other factors, as noted supra.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids. A portion or fragment of a polypeptide may be a peptide. In the case of an antibody or immunoglobulin fragment, the fragment typically binds to the target antigen.

By "fusion protein" is meant a protein generated by expression of a nucleic acid (polynucleotide) sequence engineered from nucleic acid sequences encoding at least a portion of two different (heterologous) proteins or peptides. To create a fusion protein, the nucleic acid sequences must be in the same reading frame and contain no internal stop codons. For example, a fusion protein includes an H3 influenza HA protein fused to a heterologous protein.

By "genetic vaccine" is meant an immunogenic composition comprising a polynucleotide encoding an antigen."

The terms "geographical location or geographical region" refers to preselected divisions of geographical areas of the earth, for example, by continent or other preselected territory or subdivision (e.g., the Middle East, which spans more than one continent). Examples of different geographical regions include countries (e.g., Turkey, Egypt, Iraq, Azerbaijan, China, United States); continents (e.g., Asia, Europe, North America, South America, Oceania, Africa); recognized geopolitical subdivisions (such as the Middle East); or hemispheres of the world (e.g., Northern, Southern, Eastern, or Western hemispheres).

By "H3 virus polypeptide" is meant an amino acid sequence that is at least 85% identical to an amino acid sequence of an HA antigen as set forth in FIGS. 1A-1C or a fragment thereof capable of inducing an immune response in an immunized subject. In an embodiment, an H3 virus polypeptide comprises or consists of TJ1-9 HA sequences or a fragment thereof.

By "H3 virus polynucleotide" is meant a nucleic acid molecule encoding an H3 virus polypeptide (antigen or antigen protein).

The term "Hemagglutinin (HA)" refers to a surface glycoprotein expressed by an influenza virus. HA mediates binding of the virus particle to a host cell and subsequent entry of the virus into the host cell. The nucleotide and amino acid sequences of numerous influenza HA proteins are known in the art and are publically available, such as those deposited with GenBank, see, e.g., U.S. Publication No. US 2015/0030628, Table 1). HA (along with neuraminidase (NA)) is one of the two major influenza virus antigenic proteins having antigenic determinants (epitopes) that are recognized and bound by antibodies/immunoglobulins.

By way of example, a hemagglutinin (HA) protein of an influenza H3N2 virus is a polypeptide or fragment thereof having at least about or equal to 85%, or at least about or equal to 90%, 95%, 98%, 99%, or greater, amino acid sequence identity to the amino acid sequence of Influenza A virus (A/Hong Kong/1-4/1968 (H3N2)) segment 4, complete sequence, Accession Number CY033017, as set forth below:

```
                                              (SEQ ID NO: 1)
MKTIIALSYIFCLALGQDLPGNDNSTATLCLGHHAVPNGTLVKTITDDQ

IEVTNATELVQSSSTGKICNNPHRILDGIDCTLIDALLGDPHCDVFQNE

TWDLEVERSKAFSNCYPYDVPDYASLRSLVASSGTLEFITEGFTWTGVT

QNGGSNACKRGPGSGFFSRLNWLTKSGSTYPVLNVTMPNNDNEDKLYIW

GVHHPSTNQEQTSLYVQASGRVTVSTRRSQQTIIPNIGSRPWVRGLSSR

ISIYWTIVKPGDVLVINSNGNLIAPRGYFKMRTGKSSIMRSDAPITCIS

ECITPNGSIPNDKPFQNVNKITYGACPKYVKQNTLKLATGMRNVPEKQT

RGLFGAIAGFIENGWEGMIDGWYGFRHQNSEGTGQAADLKSTQAAIDQI

NGKLNRVIEKTNEKFHQIEKEFSEVEGRIQDLEKYVEDTKIDLWSYNAE

LLVALENQHTIDLTDSEMNKLFEKTRRQLRENAEDMGNGCFKIYHKCDN

ACIESIRNGTYDHDVYRDEALNNRFQIKGVELKSGYKDWILWISFAISC

ELLCVVLLGFIMWACQRGNIRCNICI.
```

In addition, a hemagglutinin (HA) protein of an influenza H3N2 virus is encoded by a polynucleotide or fragment thereof having at least about or equal to 85%, or at least about or equal to 90%, 95%, 98%, 99%, or greater, sequence identity to the polynucleotide sequence as follows:

```
                                                         (SEQ ID NO: 2)
   1 attaatcatg aagaccatca ttgctttgag ctacattttc tgtctggctc tcggccaaga 61 ccttccagga aatgacaaca gcacagcaac gctgtgcctg ggacatcatg cggtgccaaa 121 cggaacacta gtgaaaacaa tcacagatga tcagattgaa gtgactaatg ctactgagct 181 agttcagagc tcctcaacgg ggaaaatatg caacaatcct catcgaatcc ttgatggaat 241 agactgcaca ctgatagatg ctctattggg ggaccctcat tgtgatgttt ttcaaaatga 301 gacatgggac cttttcgttg aacgcagcaa agctttcagc aactgttacc cttatgatgt 361 gccagattat gcctccctta ggtcactagt tgcctcgtca ggcactctgg agtttatcac 421 tgagggtttc acttggactg gggtcactca gaatggggga agcaatgctt gcaaaagggg 481 acctggtagc ggttttttca gtagactgaa ctggttgacc aaatcaggaa gcacatatcc 541 agtgctgaac gtgactatgc caaacaatga caattttgac aaactataca tttgggggt 601 tcaccacccg agcacgaacc aagaacaaac cagcctgtat gttcaagcat cagggagagt 661 cacagtctct accaggagaa gccagcaaac tataatcccg aatatcgggt ccagaccctg 721 ggtaaggggt ctgtctagta gaataagcat ctattggaca atagttaagc cgggagacgt 781 actggtaatt aatagtaatg ggaacctaat cgctcctcgg ggttatttca aaatgcgcac 841 tgggaaaagc tcaataatga ggtcagatgc acctattgat acctgtattt ctgaatgcat 901 cactccaaat ggaagcattc ccaatgacaa gcccttttcaa aacgtaaaca agatcacata 961 tggagcatgc cccaagtatg ttaagcaaaa caccctgaag ttggcaacag ggatgcggaa 1021 tgtaccagag aaacaaacta gaggcctatt cggcgcaata gcaggtttca tagaaaatgg 1081 ttgggaggga atgatagacg gttggtacgg tttcaggcat caaaattctg agggcacagg 1141 acaagcagca gatcttaaaa gcactcaagc agccatcgac caaatcaatg gaaattgaa 1201 cagggtaatc gagaagacga acgagaaatt ccatcaaatc gaaaaggaat tctcagaagt 1261 agaagggaga attcaggacc tcgagaaata cgttgaagac actaaaatag atctctggtc 1321 ttacaatgcg gagcttcttg tcgctctgga gaatcaacat acaattgacc tgactgactc 1381 ggaaatgaac aagctgtttg aaaaacaag gaggcaactg agggaaaatg ctgaagacat 1441 gggcaatggt tgcttcaaaa tataccacaa atgtgacaac gcttgcatag agtcaatcag 1501 aaatgggact tatgaccatg atgtatacag agacgaagca ttaaacaacc ggtttcagat 1561 caaaggtgtt gaactgaagt ctggataaca agactggatc ctgtggattt cctttgccat 1621 atcatgcttt ttgctttgtg ttgttttgct ggggttcatc atgtgggcct gccagagagg 1681 caacattagg tgcaacattt gcatttgagt gtattagtaa.
```

"Hybridization" means hydrogen bonding, which may be Watson-Crick, Hoogsteen, or reversed Hoogsteen hydrogen bonding, between complementary nucleobases. For example, in DNA, adenine and thymine, and cytosine and guanine, are, respectively, complementary nucleobases that pair through the formation of hydrogen bonds.

By "immunogen" is meant a compound, composition, or substance which is capable, under appropriate conditions, of eliciting or stimulating an immune response, such as the production of antibodies, and/or a T-cell response, in an animal, including compositions that are injected or absorbed into an animal. As used herein, an "immunogenic composition" is a composition comprising an immunogen (such as an H3 HA polypeptide) or a vaccine comprising an H3 HA polypeptide). As will be appreciated by the skilled person in the art, if administered to a subject in need prior to the subject's contracting disease or experiencing full-blown disease, an immunogenic composition can be prophylactic and result in the subject's eliciting an immune response, e.g., a neutralizing antibody and/or cellular immune response, to protect against disease, or to prevent more severe disease or condition, and/or the symptoms thereof. If administered to a subject in need following the subject's contracting disease, an immunogenic composition can be therapeutic and result in the subject's eliciting an immune response, e.g., a neutralizing antibody and/or cellular immune response, to treat the disease, e.g., by reducing, diminishing, abrogating, ameliorating, or eliminating the disease, and/or the symptoms thereof. In an embodiment, the immune response is a B cell response, which results in the production of antibodies, e.g., neutralizing antibodies, directed against the immunogen or immunogenic composition comprising the antigen or antigen sequence. In a manner similar to the foregoing, in some embodiments, an immunogenic composition or vaccine can be prophylactic. In some embodiments, an immunogenic composition or vaccine can be therapeutic. In an embodiment, the disease is influenza (flu).

The term "immune response" is meant any response mediated by an immunoresponsive cell. In one example of an immune response, leukocytes are recruited to carry out a variety of different specific functions in response to exposure to an antigen (e.g., a foreign entity). Immune responses are multifactorial processes that differ depending on the type of cells involved. Immune responses include cell-mediated responses (e.g., T cell responses), humoral responses (B cell/antibody responses), innate responses and combinations thereof.

By "immunogenic composition" is meant a composition comprising an antigen, antigen sequence, or immunogen, wherein the composition elicits an immune response in an immunized subject.

The term "immunize" (or immunization) refers to rendering a subject protected from a disease, infectious disease, or pathology, or the symptoms thereof, caused by an H3 virus, such as by vaccination.

The term "influenza virus" refers to a segmented negative-strand RNA virus that belongs to the Orthomyxoviridae family of viruses. There are three types of Influenza viruses: A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H3N2, cause systemic infections in poultry in which mortality may reach 100%.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 5%, 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid, protein, or peptide is purified if it is substantially free of cellular material, debris, non-relevant viral material, or culture medium when produced by recombinant DNA techniques, or of chemical precursors or other chemicals when chemically synthesized. Purity and homogeneity are typically determined using standard purification methods and analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. The term "isolated" also embraces recombinant nucleic acids, proteins or viruses, as well as chemically synthesized nucleic acids or peptides.

By "isolated polynucleotide" is meant a nucleic acid (e.g., a DNA molecule) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 40%, by weight, at least 50%, by weight, at least 60%, by weight, free from the proteins and naturally-occurring organic molecules with which it is naturally associated. Preferably, an isolated polypeptide preparation is at least 75%, more preferably at least 90%, and most preferably, at least 99%, by weight, free from the proteins and naturally-occurring organic molecules with which it is naturally associated. An isolated polypeptide may be obtained, for example, by extraction from a natural source; by expression of a recombinant nucleic acid encoding such a polypeptide; or by chemically synthesizing the protein. Purity can be measured by any standard, appropriate method, for example, column chromatography, polyacrylamide gel electrophoresis, or by HPLC analysis. An isolated polypeptide can refer to broadly active virus immunogen polypeptide generated by the methods described herein.

By "linker" is meant one or more amino acids that serve as a spacer between two polypeptides or peptides of a fusion protein.

By "marker" is meant any protein or polynucleotide having an alteration in expression level or activity that is associated with a disease, condition, pathology, or disorder.

A "Matrix (M1) protein" refers to an influenza virus structural protein found within the viral envelope. M1 is thought to function in assembly and budding of virus following infection of a cell.

The term "Neuraminidase (NA)" refers to an influenza virus membrane glycoprotein. NA is involved in the destruction of the cellular receptor for the viral HA by cleaving terminal sialic acid residues from carbohydrate moieties on the surfaces of infected cells. NA also cleaves sialic acid residues from viral proteins, preventing aggregation of viruses. NA (along with HA) is one of the two major influenza virus antigenic determinants.

As used herein, "obtaining" as in "obtaining an agent" includes synthesizing, isolating, purchasing, or otherwise acquiring the agent.

The term "operably linked" refers to nucleic acid sequences as used herein. By way of example, a first nucleic acid sequence is operably linked to a second nucleic acid sequence when the first nucleic acid sequence is placed in a functional relationship with the second nucleic acid sequence. For instance, a promoter is operably linked to a coding sequence if the promoter affects (allows) the transcription or expression of the coding sequence. Generally, operably linked DNA sequences are contiguous and, where necessary to join two protein-coding regions, are in the same reading frame.

An influenza HA protein that is "computationally optimized" generally reflects an HA protein sequence resulting from the comparison of sequences (amino acid sequences) from two or more viruses, such as, for example, sequences of clades of H3 influenza viruses, such as described, for example, in US Patent Application Publication US 2015/0030628. The nucleotide sequence encoding an H3 HA protein generated by the described methods can be optimized for expression in mammalian cells via codon-optimization and RNA optimization (such as to increase RNA stability) using procedures and techniques practiced in the art.

A broadly reactive, pan-epitopic immunogen, such as H3 influenza hemagglutinin (HA) protein, for eliciting an immune response in a subject possesses a collective set of strongly immunogenic epitopes (also called antigenic determinants). An H3 virus HA protein described herein is a "pan-epitopic" H3 immunogen that is suitable for use as a vaccine, which elicits a broadly reactive immune response, e.g., a neutralizing antibody response, against a plurality of H3 virus types which express HA proteins on the viral surface, when introduced into a host subject, in particular, a human subject infected with H3 virus. The immunogenic antigen (or vaccine) is advantageous for providing an anti-H3 virus immunogen (or a vaccine) that elicits a broadly active immune response against H3 influenza virus HA antigens with antigenic variability and similarity, and treats or protects against infection and disease caused by more than one H3 influenza virus subtype.

By "open reading frame (ORF)" is meant a series of nucleotide triplets (codons) that code for amino acids without any termination codons. These sequences are usually translatable into a peptide or polypeptide.

As used herein, an influenza virus "outbreak" refers to a collection of virus isolates from within a geographical location (e.g., within a single country) in a given period of time (e.g., in a year).

The term "pharmaceutically acceptable vehicle" refers to conventional carriers (vehicles) and excipients that are physiologically and pharmaceutically acceptable for use, particularly in mammalian, e.g., human, subjects. Such pharmaceutically acceptable vehicles are known to the skilled practitioner in the pertinent art and can be readily found in *Remington's Pharmaceutical Sciences*, by E. W. Martin, Mack Publishing Co., Easton, Pa., 15th Edition (1975) and its updated editions, which describes compositions and formulations suitable for pharmaceutical delivery of one or more therapeutic compositions, such as one or more influenza vaccines, and additional pharmaceutical agents. In general, the nature of a pharmaceutically acceptable carrier depends on the particular mode of administration being employed. For instance, parenteral formulations usually comprise injectable fluids/liquids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers may include, for example, pharmaceutical grades of mannitol, lactose, starch, or magnesium stearate, which typically stabilize and/or increase the half-life of a composition or drug. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

By "plasmid" is meant a circular nucleic acid molecule capable of autonomous replication in a host cell.

By "polypeptide" (or protein) is meant a polymer in which the monomers comprise amino acid residues that are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" also refers to an amino acid that is incorporated into a protein, polypeptide, or peptide.

Conservative amino acid substitutions are those substitutions that, when made, least interfere with the properties of the original protein, that is, the structure and especially the function of the protein is conserved and is not significantly changed by such substitutions. Examples of conservative amino acid substitutions are known in the art, e.g., as set forth in, for example, U.S. Publication No. 2015/0030628. Conservative substitutions generally maintain (a) the structure of the polypeptide backbone in the area of the substitution, for example, as a sheet or helical conformation; (b) the charge or hydrophobicity of the molecule at the target site; and/or (c) the bulk of the side chain The substitutions that are generally expected to produce the greatest changes in protein properties are non-conservative, for instance, changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "promoter" is meant an array of nucleic acid control sequences, which direct transcription of a nucleic acid. A promoter includes necessary nucleic acid sequences near the start site of transcription. A promoter also optionally includes distal enhancer or repressor sequence elements. A "constitutive promoter" is a promoter that is continuously active and is not subject to regulation by external signals or molecules. In contrast, the activity of an "inducible promoter" is regulated by an external signal or molecule (for example, a transcription factor). By way of example, a promoter may be a CMV promoter.

As will be appreciated by the skilled practitioner in the art, the term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to routine methods, such as fractionation, chromatography, or electrophoresis, to remove various components of the initial preparation, such as proteins, cellular debris, and other components.

A "recombinant" nucleic acid, protein or virus is one that has a sequence that is not naturally occurring or that has a sequence that is made by an artificial combination of two otherwise separated segments of sequence. Such an artificial combination is often accomplished by chemical synthesis or by the artificial manipulation of isolated segments of nucleic acids, for example, by genetic engineering techniques. A "non-naturally occurring" nucleic acid, protein or virus is one that may be made via recombinant technology, artificial manipulation, or genetic or molecular biological engineering procedures and techniques, such as those commonly practiced in the art.

By "reduces" is meant a negative alteration of at least 5%, 10%, 25%, 30%, 40%, 50%, 75%, 80%, 85%, 90%, 95%, 98%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide, such as a virus polypeptide, peptide, or vaccine product, but which does not substantially recognize and bind other molecules in a sample, for example, a biological sample, which naturally includes a polypeptide, such as a virus polypeptide or peptide.

Nucleic acid molecules useful in the methods described herein include any nucleic acid molecule that encodes a polypeptide as described, or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pairing to form a double-stranded molecule between complementary polynucleotide sequences (e.g., a gene), or portions thereof, under various conditions of stringency. (See, e.g., Wahl, G. M. and S. L. Berger, (1987), *Methods Enzymol.*, 152:399; Kimmel, A. R., (1987), *Methods Enzymol.* 152:507).

By way of example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (*Proc. Natl. Acad. Sci., USA* 72:3961, 1975); Ausubel et al. (*Current Protocols in Molecular Biology*, Wiley Interscience, New York, 2001); Berger and Kimmel (*Guide to Molecular Cloning Techniques*, 1987, Academic Press, New York); and Sambrook et al., *Molecular Cloning: A Laboratory Manual*, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, or at least 80% or 85%, or at least or equal to 90%, 95% or even 99% identical at the amino acid level or nucleic acid to the sequence used for comparison.

"Sequence identity" refers to the similarity between amino acid or nucleic acid sequences that is expressed in terms of the similarity between the sequences. Sequence identity is frequently measured in terms of percentage identity (or similarity or homology); the higher the percentage, the more similar the sequences are. Homologs or variants of a given gene or protein will possess a relatively high degree of sequence identity when aligned using standard methods. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence. In addition, other programs and alignment algorithms are described in, for example, Smith and Waterman, 1981, *Adv. Appl. Math.* 2:482; Needleman and Wunsch, 1970, *J. Mol. Biol.* 48:443; Pearson and Lipman, 1988, *Proc. Natl. Acad. Sci. U.S.A.* 85:2444; Higgins and Sharp, 1988, *Gene* 73:237-244; Higgins and Sharp, 1989, *CABIOS* 5:151-153; Corpet et al., 1988, *Nucleic Acids Research* 16:10881-10890; Pearson and Lipman, 1988, *Proc. Natl. Acad. Sci. U.S.A.* 85:2444; and Altschul et al., 1994, *Nature Genet.* 6:119-129. The NCBI Basic Local Alignment Search Tool (BLAST™) (Altschul et al. 1990, *J. Mol. Biol.* 215:403-410) is readily available from several sources, including the National Center for Biotechnology Information (NCBI, Bethesda, Md.) and on the Internet, for use in connection with the sequence analysis programs blastp, blastn, blastx, tblastn and tblastx.

By "subject" is meant an animal, e.g., a mammal, including, but not limited to, a human, a non-human primate, or a non-human mammal, such as a bovine, equine, canine, ovine, or feline mammal, or a sheep, goat, llama, camel, or a rodent (rat, mouse), gerbil, or hamster. In a nonlimiting example, a subject is one who is infected with an H3 virus, or who is at risk of infection by such virus, or who is susceptible to such infection. In particular aspects as described herein, the subject is a human subject, such as a patient.

Ranges provided herein are understood to be shorthand for all of the values within the range, inclusive of the first and last stated values. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or greater, consecutively, such as to 100 or greater.

As used herein, the terms "treat," treating," "treatment," and the like refer to reducing, diminishing, decreasing, abrogating, ameliorating, or eliminating, a disease, condition, disorder, or pathology, and/or symptoms associated therewith. While not intending to be limiting, "treating" typically relates to a therapeutic intervention that occurs after a disease, condition, disorder, or pathology, and/or symptoms associated therewith, have begun to develop so as to reduce the severity of the disease, etc., and the associated signs and symptoms. It will be appreciated that, although not precluded, treating a disorder or condition does not require that the disease, condition, disorder, pathology, or the symptoms associated therewith, be completely eliminated.

As used herein, the terms "prevent," "preventing," "prevention," "prophylactic treatment" and the like, refer to inhibiting or blocking a disease state, or the full development of a disease in a subject, or reducing the probability of developing a disease, disorder or condition in a subject, who does not have, but is at risk of developing, or is susceptible to developing, a disease, disorder, or condition.

As referred to herein, a "transformed" cell is a cell into which a nucleic acid molecule or polynucleotide sequence has been introduced by molecular biology techniques. As used herein, the term "transformation" encompasses all techniques by which a nucleic acid molecule or polynucleotide may be introduced into such a cell, including transfection with viral vectors, transformation with plasmid vectors, and introduction of naked nucleic acid (DNA or RNA) by electroporation, lipofection, and particle gun acceleration.

By "vaccine" is meant a preparation of immunogenic material (e.g., protein or nucleic acid; vaccine) capable of stimulating (eliciting) an immune response, administered to a subject to treat a disease, condition, or pathology, or to prevent a disease, condition, or pathology, such as an infectious disease (caused by H3 virus infection, for example). The immunogenic material may include, for example, attenuated or killed microorganisms (such as attenuated viruses), or antigenic proteins, peptides or DNA derived from such microorganisms. Vaccines may elicit a prophylactic (preventative) immune response in the subject; they may also elicit a therapeutic response immune response in a subject. As mentioned above, methods of vaccine administration vary according to the vaccine, and can include routes or means, such as inoculation (intravenous or subcutaneous injection), ingestion, inhalation, or other forms of administration. Inoculations can be delivered by any of a number of routes, including parenteral, such as intravenous, subcutaneous or intramuscular. Vaccines may also be administered with an adjuvant to boost the immune response.

As used herein, a "vector" refers to a nucleic acid (polynucleotide) molecule into which foreign nucleic acid can be inserted without disrupting the ability of the vector to replicate in and/or integrate into a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes in a host cell. In some embodiments of the present disclosure, the vector encodes an influenza HA, NA or M1 protein. In some embodiments, the vector is the pTR600 expression vector (U.S. Patent Application Publication No. 2002/0106798; Ross et al., 2000, *Nat Immunol.* 1 (2): 102-103; and Green et al., 2001, *Vaccine* 20:242-248).

By "virus-like particle (VLP)" is meant virus particles made up of one of more viral structural proteins, but lacking the viral genome. Because VLPs lack a viral genome, they are non-infectious and yield safer and potentially more-economical vaccines and vaccine products. In addition, VLPs can often be produced by heterologous expression and can be easily purified. Most VLPs comprise at least a viral core protein that drives budding and release of particles from a host cell. One example of such a core protein is influenza M1. In some embodiments herein, an H3 influenza VLP comprises the HA, NA and M1 proteins. As described herein, H3 influenza VLPs can be produced by transfection of host cells with plasmids encoding the H3 HA, NA and M1 proteins. After incubation of the transfected cells for an appropriate time to allow for protein expression (such as for approximately 72 hours), VLPs can be isolated from cell culture supernatants. By way of example, a protocol for purifying or isolating influenza VLPs from cell supernatants involves low speed centrifugation (to remove cell debris), vacuum filtration and ultracentrifugation of the VLPs through 20% glycerol. A virus-like particle may also include a subviral particle (SVP), which is typically smaller in size than a virus and constitutes a particle without a virus capsid or genome.

Unless specifically stated or obvious from context, as used herein, the term "or" is understood to be inclusive. Unless specifically stated or obvious from context, as used herein, the terms "a", "an", and "the" are understood to be singular or plural. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Unless specifically stated or obvious from context, as used herein, the term "about" is understood as within a range of normal tolerance in the art, for example within 2 standard deviations of the mean. About may be understood as being within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1C show the amino acid sequences of nine representative HA polypeptides (proteins) of the H3 influenza A virus strain, referred to TJ1-9 HA herein, that are broadly reactive immunogens that elicit an immune response against H3 virus and H3 virus HA protein. Nucleic acid sequences encoding these polypeptides can be used to generate virus-like particles (VLPs) containing the H3 protein antigens, which are used as immunogens/vaccines to generate neutralizing antibodies in immunized subjects. As shown in FIGS. 1A-1C, the full-length TJ1-9 HA polypeptides (SEQ ID NOs: 3-11) are 566 amino acids in length. Specifically, the amino acid sequence of TJ-1 is set forth in SEQ ID NO: 3; the amino acid sequence of TJ-2 is set forth in SEQ ID NO: 4; the amino acid sequence of TJ-3 is set forth in SEQ ID NO: 5; the amino acid sequence of TJ-4 is set forth in SEQ ID NO: 6; the amino acid sequence of TJ-5 is set forth in SEQ ID NO: 7; the amino acid sequence of TJ-6 is set forth in SEQ ID NO: 8; the amino acid sequence of TJ-7 is set forth in SEQ ID NO: 9; the amino acid sequence of TJ-8 is set forth in SEQ ID NO: 10; the amino acid sequence of TJ-9 is set forth in SEQ ID NO: 11.

FIG. 2A shows graphs of hemagglutination inhibition (HAI) titers of serum antibodies generated against VLPs produced from the TJ-2, TJ-3, TJ-5, TJ-6, TJ-7, TJ-8 and TJ-9 HA sequences ("TJ" VLPs) as described herein (presented in FIGS. 1A-1C) and used as immunogens (vaccines). The antibodies produced against the several TJ VLPs were broadly reactive against different historical strains of H3 viruses (x-axis). The HAI assay was carried out using serum obtained from immunized mice bled on Day 77, 0.75% guinea pig red blood cells and 20 nM Oseltamivir (Tamiflu). FIG. 2B shows the results of HAI assays using VLPs containing other H3 HA sequences (e.g., Bris/07, Perth/09, Vic/11, Tx/12, Switz/13, HK/14). FIG. 2C shows the results of HAI assays using a PBS control.

DETAILED DESCRIPTION OF THE INVENTION

Figure 2A:
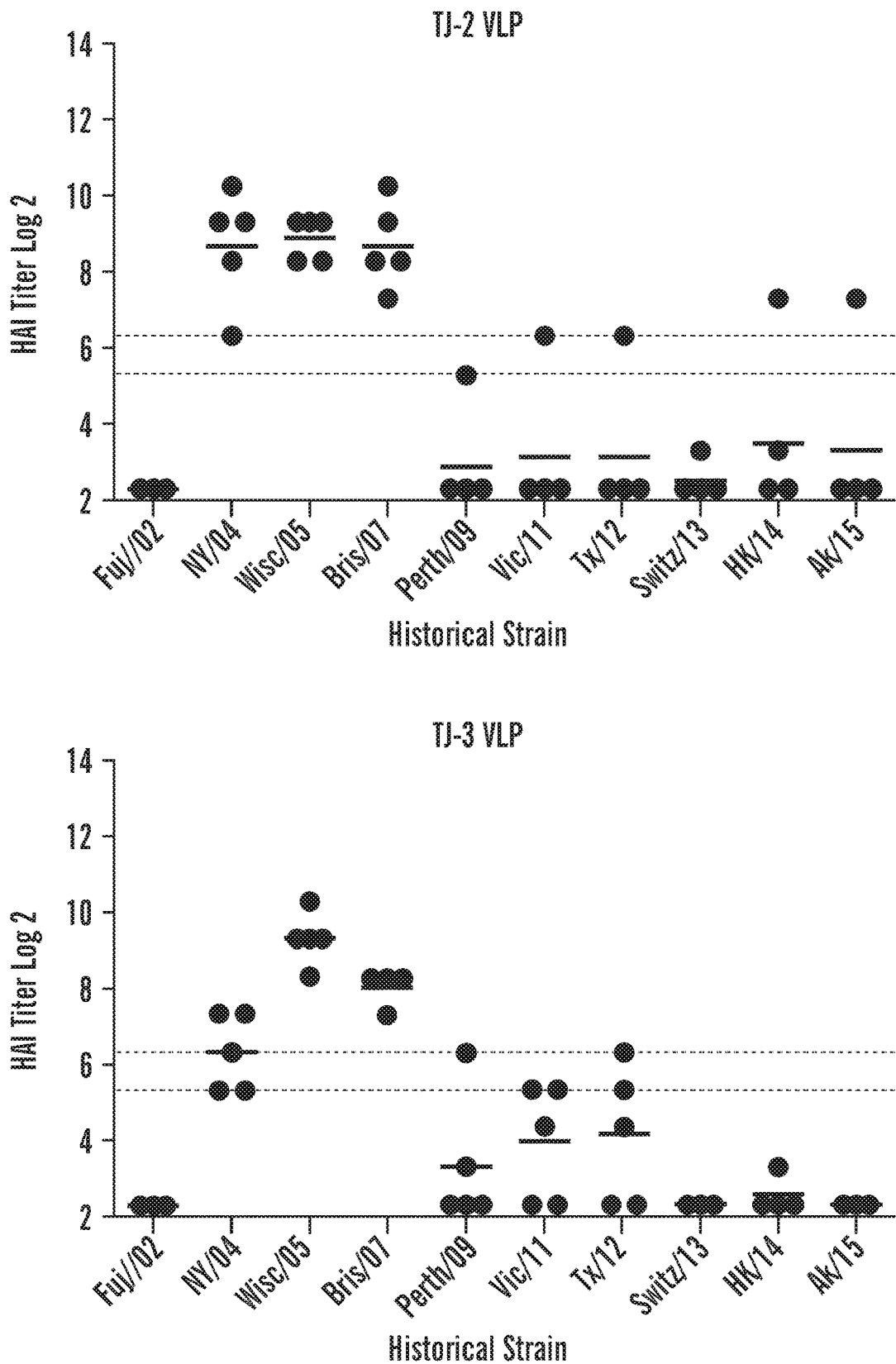
FIGS. 2A-2C present graphs showing hemagglutination inhibition (HAI) titers of serum antibodies generated against different H3 virus HA protein-derived VLPs used as immunogens (vaccines), following incubation of the sera (e.g., mouse sera) with different strains of H3 virus (Historical Strain) in an HAI assay.
Figure 2A:
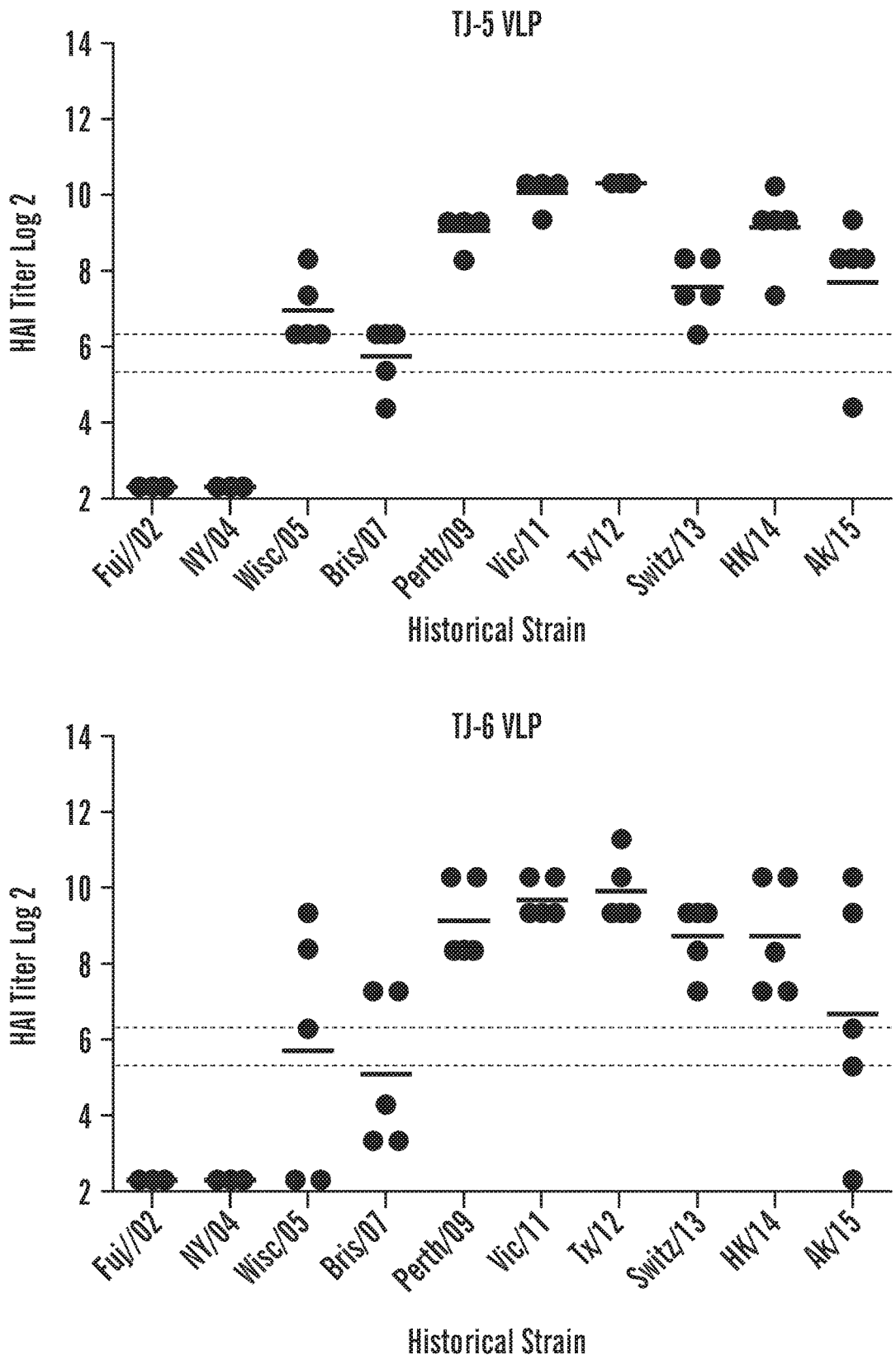
Figure 2A:
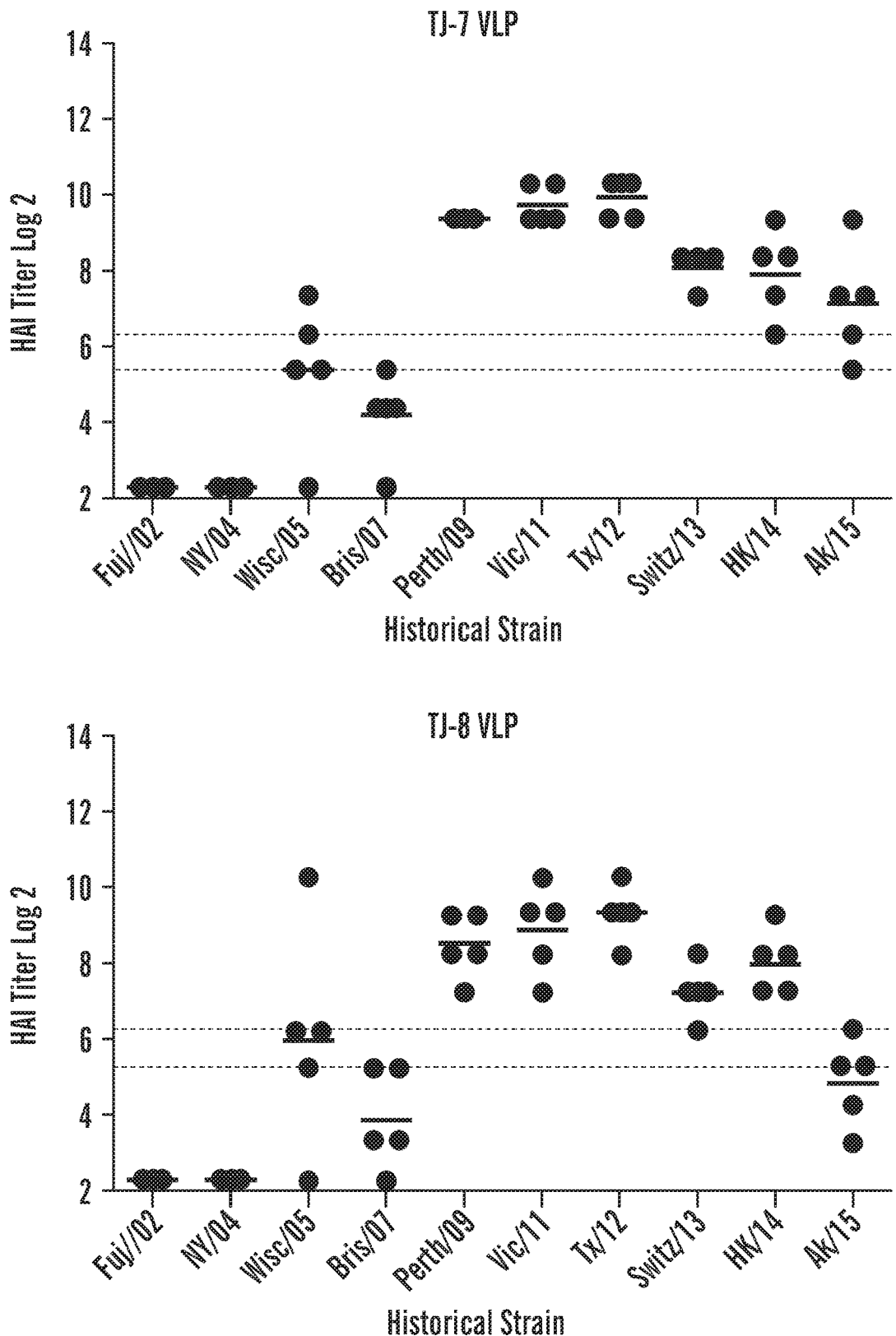
Figure 2A:
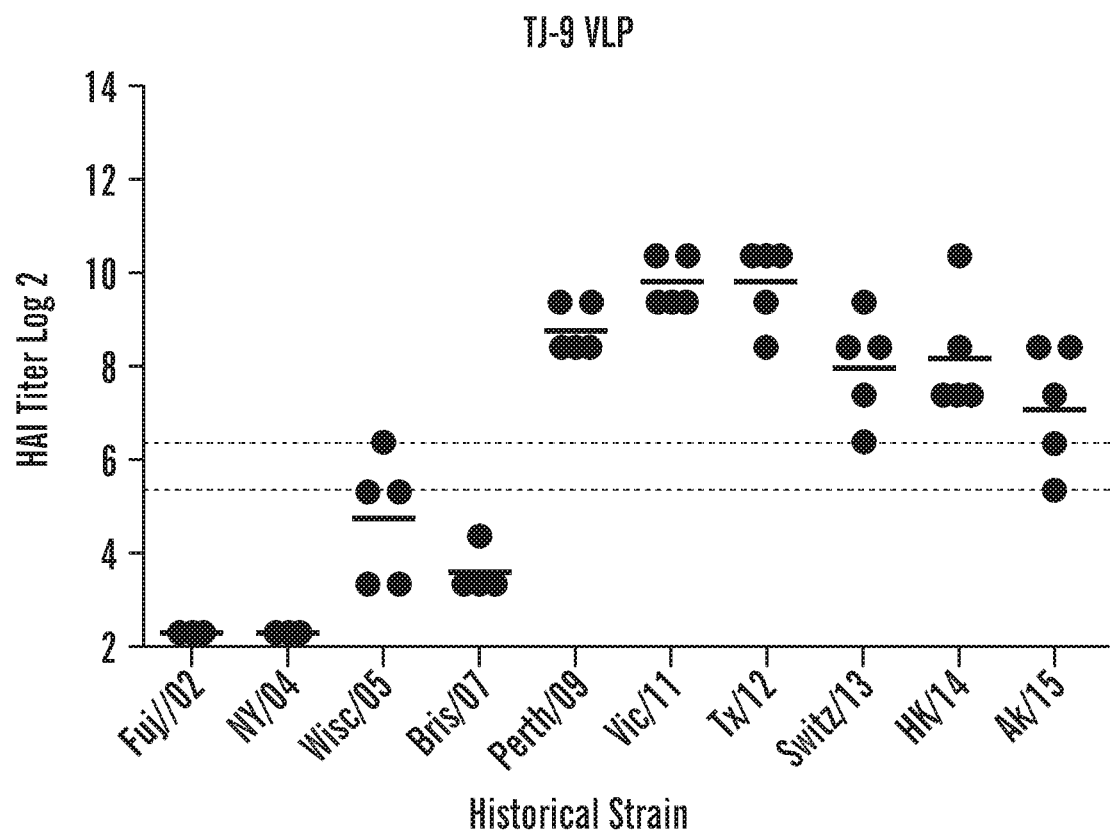

The H3 influenza virus routinely spreads in humans and causes seasonal flu epidemics. The H3 virus typically causes severe flu disease and adapts to evade being eradicated by constantly changing its surface proteins, such as the HA protein. H3 influenza A virus was found to be a dominant strain in the U.S. and worldwide, e.g., in Australia and the United Kingdom, in the flu season that extended from the year 2017 into 2018. The H3 strain was particularly problematic to treat because of its unusually high rate of mutation and an inability to generate vaccines that were effective against the relatively rapid changes that occurred in its HA surface protein, such as during production of a vaccine against this strain.

Featured herein are synthetic (non-naturally occurring), immunogenic antigens, e.g., protein and glycoprotein antigens, derived from the influenza ("flu") hemagglutinin (HA) protein of the H3 strain of influenza A virus, that elicit a potent, broadly reactive and long-lasting immune response in a subject, particularly, a human subject. Such immunogenic antigens are also referred to as "immunogens" herein.

Provided are immunogens that protect against disease caused by the influenza H3 strain, or seasonal influenza H3 strains, spanning several years, including drifted strains not yet in existence. In an embodiment, fully synthetic protein antigens are featured, such as influenza H3 virus HA protein antigens. Such H3 HA antigens are synthetic proteins not found in nature, yet they retain all of the functions of a natural H3 HA viral protein and are immunogenic, i.e., they can elicit an immune response, in particular, a broadly active immune response in the form of neutralizing antibodies and/or reactive T lymphocytes, following administration or delivery to, or introduction into, a subject. Also provided are immunogenic compositions, e.g., vaccines, comprising the synthetic H3 virus protein antigens, or nucleic acids encoding the antigens.

An H3 HA amino acid sequence and a protein antigen having such sequence are particularly for use as an immunogen, or in an immunogenic composition, e.g., a vaccine, that elicits a broadly reactive immune response in a subject, particularly a human subject, to whom the composition, or vaccine, is administered. The H3 virus immunogens comprise antigenic determinants that represent different "antigenic spaces" that are derived from the sequences of many H3 virus strains analyzed based on seasonal periods of time (either overlapping or non-overlapping seasonal time periods). Such overlapping or non-overlapping seasonal time periods may encompass different intervals of time, for example, 5 months, 6 months, 7 months, eight months, nine months, 10 months, 11 months, 1 year, 2 years, 3 years, 4 years, 5 years, 6 years, 7 years, 8 years, 10 years or more, including time intervals therebetween.

The H3 virus antigens described herein embrace seasonal, pan-epitopic, broadly reactive antigens of H3 influenza virus and subtypes thereof, especially antigens containing sequences based on H3 drift variants, wherein the antigens are designed to generate a broadly active immune response, particularly in the form of neutralizing antibodies, in a subject, particularly a human subject. Such antigens are beneficial as immunogens, which elicit an immune response (e.g., production of neutralizing antibodies) against the H3 virus where multiple strains of H3 co-circulate at one time. The broadly reactive H3 immunogenic antigens can be derived from H3 virus that frequently mutates parts of its genome to escape immune pressure, and as a consequence, evades immune surveillance in a subject whose immune system is not primed or stimulated to generate antibodies against antigenic epitopes (determinants) on the H3 antigens following infection. Thus, the synthetic H3 antigens, e.g., H3 HA antigen, comprise amino acid (or polynucleotide) sequences that will elicit greater numbers of neutralizing antibodies against potential H3 drift variants within and across multiple seasons compared with wild-type antigen sequences.

An H3 HA immunogenic protein, or immunogen, as described herein can be employed in an immunogenic composition or as a vaccine that may afford protection against many H3 virus strains over several years. The broadly reactive H3 influenza immunogens and vaccines described herein are advantageous in that they are designed to provide broader and longer-lasting protection against several seasonal H3 flu strains (or clades) prevalent in different geographical locations. Provided by the immunogens and their sequences as described herein is a universal and broad-spectrum H3 flu vaccine that may alleviate the need for a seasonal flu vaccine (immunogenic composition) against the H3 strain and subtypes of influenza virus that is administered annually.

The immunogenic H3 virus HA antigens described herein may be used in immunogenic compositions (e.g., influenza vaccines) that are capable of affording protective immunity against H3 influenza infection and disease in a subject. The protective immunity is provided in the subject through the elicitation of potent, broadly reactive, anti-H3 HA specific antibody responses that protect the subject against drifted, seasonal H3 influenza virus strains and pandemic H3 influenza virus strains. The immunogenic compositions and vaccines provide an advantage over prior and traditional immunogenic compositions and vaccines directed against H3 virus, which typically depend on the selection of candidate vaccine viruses by public health authorities following analysis of data collected through active surveillance of influenza viruses circulating each year.

Influenza Virus

Influenza viruses are segmented negative-strand RNA viruses that belong to the Orthomyxoviridae family. There are three types of Influenza viruses: A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as H3, cause systemic infections in poultry in which mortality may reach 100%. Animals infected with influenza A often act as a reservoir for the influenza viruses and certain subtypes have been shown to cross the species barrier to humans in whom they can cause severe disease and devastating flu outbreaks that can lead to death of the infected human subjects.

Influenza A viruses can be classified into subtypes based on allelic variations in antigenic regions of two genes that encode surface glycoproteins, namely, hemagglutinin (HA) and neuraminidase (NA) which are required for viral attachment and cellular release. Currently, sixteen subtypes of HA (H1-H16) and nine NA (N1-N9) antigenic variants are known for influenza A virus. Previously, only three subtypes were known to circulate in humans (H1N1, H1N2, and H3N2). However, in recent years, for example, the pathogenic H5N1 subtype of avian influenza A has been reported to cross the species barrier and infect humans as documented in Hong Kong in 1997 and 2003, leading to the death of several patients.

In humans, the avian influenza virus infects cells of the respiratory tract as well as the intestinal tract, liver, spleen, kidneys and other organs. Symptoms of avian influenza infection include fever, respiratory difficulties, including shortness of breath and cough, lymphopenia, diarrhea and difficulties regulating blood sugar levels. In contrast to seasonal influenza, the group most at risk is healthy adults which make up the bulk of the population. Due to the high pathogenicity of certain avian influenza A subtypes, particularly H3, and their demonstrated ability to cross over to infect humans, there is a significant economic and public health risk associated with these viral strains, including a real epidemic and pandemic threat.

The influenza A virus genome encodes nine structural proteins and one nonstructural (NS1) protein with regulatory functions. The influenza virus segmented genome contains eight negative-sense RNA (nsRNA) gene segments (PB2, PB1, PA, NP, M, NS, HA and NA) that encode at least ten polypeptides, including RNA-directed RNA polymerase proteins (PB2, PB 1 and PA), nucleoprotein (NP), neuraminidase (NA), hemagglutinin, e.g., subunits HA1, frequently referred to as the "head" subunit; and HA2, frequently referred to as the "tail" or "stalk" subunit; the matrix proteins (M1 and M2); and the non-structural proteins (NS1 and NS2) (See, e.g., Krug et al., 1989, *In: The Influenza Viruses*, R. M. Krug, ed., Plenum Press, N.Y., pp. 89 152).

The ability of influenza virus, e.g., H3, to cause widespread disease is due to its ability to evade the immune system by undergoing antigenic change, which is believed to occur when a host is infected simultaneously with both an animal influenza virus and a human influenza virus. During mutation and reassortment in the host, the virus may incorporate an HA and/or NA surface protein gene from another virus into its genome, thereby producing a new influenza subtype and evading the immune system.

Because of antigenic variation (drift) in the circulating strains of H3 influenza virus, in particular, in the HA and NA proteins of the virus, the efficacy of vaccines against H3 influenza virus has frequently been less than optimal and sub-par. The methods described herein provide broadly reactive, pan-epitopic HA or NA antigens of H3 influenza virus that generate a broadly reactive immune response, particularly, in the form of neutralizing antibodies that bind to the H3 viral antigens and neutralize the activity of the virus (e.g., its ability to infect cells), to treat H3 influenza and its symptoms more effectively.

Influenza Virus Hemagglutinin (HA) and Neuraminidase (NA) Proteins

HA is a viral surface glycoprotein that generally comprises approximately 560 amino acids (e.g., 566 amino acids) and represents 25% of the total virus protein. As described herein, HA is a protein antigen that is highly useful as an immunogen against the H3 virus because it contains a diverse repertoire of epitopes against which antibodies are generated in a subject or host that encounters the H3 HA antigen during infection.

HA is responsible for adhesion of the viral particle to, and its penetration into, a host cell, particularly, in the respiratory epithelium, in the early stages of infection. Cleavage of the virus HA0 precursor into the HAI and HA2 sub-fragments is a necessary step in order for the virus to infect a cell. Thus, cleavage is required in order to convert new virus particles in a host cell into virions capable of infecting new cells. Cleavage is known to occur during transport of the integral HA0 membrane protein from the endoplasmic reticulum of the infected cell to the plasma membrane. In the course of transport, HA undergoes a series of co- and post-translational modifications, including proteolytic cleavage of the precursor HA into the amino-terminal fragment HAI ("head") and the carboxy terminal HA2 ("tail" or "stalk"). One of the primary difficulties in growing H3 influenza strains in primary tissue culture or established cell lines arises from the requirement for proteolytic cleavage activation of the influenza hemagglutinin in the host cell.

Although it is known that an uncleaved HA can mediate attachment of the virus to its neuraminic acid-containing receptors on a cell surface, it is not capable of the next step in the infectious cycle, which is fusion. It has been reported that exposure of the hydrophobic amino terminus of HA2 by cleavage is required so that it can be inserted into the target cell, thereby forming a bridge between the virus and the target cell membranes. This process is followed by fusion of the two membranes and entry of the virus into the target cell.

Proteolytic activation of HA involves cleavage at an arginine residue by a trypsin-like endoprotease, which is often an intracellular enzyme that is calcium-dependent and has a neutral pH optimum. Since the activating proteases are cellular enzymes, the infected cell type determines whether the HA is cleaved. The HA of the mammalian influenza viruses and the nonpathogenic avian influenza viruses are susceptible to proteolytic cleavage only in a restricted number of cell types. There are also differences in host range resulting from differences in hemagglutinin cleavability which are correlated with the pathogenic properties of the virus.

Neuraminidase (NA) is a second membrane glycoprotein of the influenza viruses. The presence of viral NA has been shown to be important for generating a multi-faceted protective immune response against an infecting virus. For most influenza A viruses, NA is 413 amino acid in length, and is encoded by a gene of 1413 nucleotides. Nine different NA subtypes have been identified in influenza viruses (N1, N2, N3, N4, N5, N6, N7, N8 and N9), all of which have been found among wild birds. NA is involved in the destruction of the cellular receptor for the viral HA by cleaving terminal neuraminic acid (also called sialic acid) residues from carbohydrate moieties on the surfaces of infected cells. NA also cleaves sialic acid residues from viral proteins, preventing aggregation of viruses. Using this mechanism, it is hypothesized that NA facilitates the release of viral progeny by preventing newly formed viral particles from accumulating along the cell membrane, as well as by promoting transportation of the virus through the mucus present on the mucosal surface. NA is an important antigenic determinant that is subject to antigenic variation.

In addition to the surface proteins HA and NA, H3 influenza virus comprises six additional internal genes, which give rise to eight different proteins, including polymerase genes PB1, PB2 and PA, matrix proteins M1 and M2, nucleoprotein (NP), and non-structural proteins NS1 and NS2 (See, e.g., Horimoto et al., 2001, *Clin Microbiol Rev.* 14 (1): 129-149).

In order to be packaged into progeny virions, H3 viral RNA is transported from the nucleus as a ribonucleoprotein (RNP) complex composed of the three influenza virus polymerase proteins, the nucleoprotein (NP), and the viral RNA, in association with the influenza virus matrix 1 (M1) protein and nuclear export protein (Marsh et al., 2008, *J Virol*, 82:2295-2304). The M1 protein that lies within the envelope is thought to function in assembly and budding. A limited number of M2 proteins are integrated into the virions (Zebedee, 1988, *J. Virol.* 62:2762-2772). These M2 proteins form tetramers having H+ ion channel activity, and when activated by the low pH in endosomes, acidify the inside of the virion, thus facilitating its uncoating (Pinto et al., 1992, (el/69:517-528). Amantadine is an anti-influenza drug that prevents viral infection by interfering with M2 ion channel activity, thus inhibiting virus uncoating.

NS1, a nonstructural protein, has multiple functions, including regulation of splicing and nuclear export of cellular mRNAs as well as stimulation of translation. The major function of NS1 seems to be to counteract the interferon activity of the host, since an NS1 knockout virus was viable, although it grew less efficiently than the parent virus in interferon-nondefective cells (Garcia-Sastre, 1998, *Virology* 252:324-330).

The NS2 nonstructural protein has been detected in virus particles (Richardson et al., 1991, *Arch. Virol.* 116:69-80; Yasuda et al., 1993, *Virology* 196:249-255). The average number of NS2 proteins in a virus particle was estimated to be 130-200 molecules. An in vitro binding assay has demonstrated direct protein-protein contact between M1 and NS2. NS2-M1 complexes have also been detected by immunoprecipitation in virus-infected cell lysates. The NS2 protein is thought to play a role in the export of the RNP from the nucleus through interaction with M1 protein (Ward et al., 1995, *Arch. Virol.* 140:2067-2073).

Broadly Reactive Influenza Proteins and Virus-Like Particles (VLPs)

Provided are non-naturally occurring, broadly reactive, pan-epitopic H3 influenza HA immunogenic polypeptides (immunogens) and influenza virus-like particles (VLPs) comprising an H3 HA immunogen containing diverse epitopes (antigenic determinants) that endow the HA antigen with the ability to generate a broadly active immune response against influenza and its symptoms, either prophylactic or therapeutic, following administration and delivery to a susceptible subject. By way of example, representative H3 HA immunogenic antigen sequences generated by the practice of methods described herein are presented in FIGS. 1A-1C herein. In particular examples, the broadly reactive, pan-epitopic H3 HA polypeptides are administered as part of a VLP.

It will be understood that the H3 influenza virus immunogens and sequences described and provided herein are non-naturally occurring, broadly reactive and pan-epitopic, whether or not these characteristics and features are explicitly stated. It will also be appreciated that the H3 antigen proteins, e.g., HA, HA1, or HA2, as described herein and used as immunogens are non-naturally occurring or synthetic antigens that elicit an immune response, e.g., neutralizing antibodies, in a subject.

The broadly reactive and immunogenic H3 antigen sequences that are capable of generating an immune response against H3 influenza virus strains, including present and future H3 virus, may be generated by a method such as described in co-pending provisional patent application No. 62/697,803, filed on Jul. 13, 2018, the contents of which are incorporated herein by reference, and which involves a consideration of the parameters of H3 antigen sequences, e.g., HA antigen sequences, from a time span or range (e.g., a linear time range), such as one or more flu seasons, and geographical location(s) in which the H3 virus was isolated, such as, for example, the Southern or Northern Hemisphere.

In an embodiment, the H3 influenza VLPs include the viral HA proteins. In embodiments, the VLPs may include the HAI and/or the HA2 proteins. It will be appreciated that in some cases, H3 influenza virus VLPs may include the viral NA and M1 proteins. The production of influenza VLPs has been described in the art and is within the skill and expertise of one of ordinary skill in the art. Briefly, and as described, influenza VLPs can be produced by transfection of host cells with one or more plasmids containing polynucleotide sequences that encode the HA, NA and M1 proteins. After incubation of the transfected cells for an appropriate time to allow for protein expression (such as for approximately 72 hours), H3 VLPs can be isolated from cell culture supernatants. H3 influenza VLPs can be purified from cell supernatants using procedures practiced in the art, for example, VLPs can isolated by low speed centrifugation (to remove cell debris), vacuum filtration and ultracentrifugation through 20% glycerol.

The influenza VLPs can be used as immunogenic compositions or influenza vaccines to elicit an immune response against H3 influenza viruses. In particular, the component, broadly reactive, pan-epitopic H3 influenza HA polypeptides of the immunogenic compositions or vaccines (or VLPs) contain antigenic (pan-epitopic) determinants that are broadly reactive and serve to elicit an immune response in a subject (e.g., the production of neutralizing antibodies and/or activated T-cells) that can treat an H3 virus-infected subject (e.g., neutralize the infecting virus) and/or protect a subject against full-blown virus infection or the signs and symptoms thereof.

In an embodiment, the antigen sequence of a broadly reactive and immunogenic H3 influenza antigen as described herein, such as an H3 HA antigen, contains a diverse repertoire of epitopic determinants that can reflect antigenic drift and sequence variability in the H3 virus's antigenic proteins, for example, over seasons (time) and in different geographic locations. In particular, an H3 virus HA antigen as described herein can comprise an amino acid sequence that contains antigenic determinants (epitopes) derived from sequence diverse influenza virus strains, including drift variants, against which broadly reactive neutralizing antibodies can be raised, especially when the antigen is used as an immunogenic product, (an immunogen), e.g., an antiviral vaccine, that is introduced into a subject.

In an aspect, the H3 viral antigen amino acid sequences provide a composite, immunogenic antigen sequence, which includes epitopic determinants ultimately derivable from both past and more recent seasons of virus infection or disease, and/or from viruses in different geographical locales, and/or from different subtypes or clades of H3 viruses, i.e., a "pan-epitopic" antigen that elicits a broadly reactive immune response when used as an immunogen, a vaccine, or a VLP. In an embodiment, the immunogenic H3 virus HA antigen sequences encompass epitopes that result from antigenic changes in the sequences of H3 HA surface antigens that arise from point mutations during viral replication, giving rise to new H3 influenza variants. As a result, the administration to a subject of an H3 immunogen as described herein can elicit a broadly reactive immune response in the subject that is directed against epitopes reflecting such antigenic changes.

Because the broadly reactive H3 HA antigens and the sequences thereof as described herein and used as an immunogen or immunogenic composition, such as a vaccine, elicit a broadly reactive immune response in an immunocompetent subject, they provides a superior vaccine that captures the antigenic epitopes of many different H3 influenza isolates (subtypes or strains), against which broadly active immune responses (e.g., broadly active neutralizing antibodies) are generated. It is noted that the terms "broadly active" and "broadly reactive" are used synonymously herein.

In an embodiment, the H3 virus antigen as described herein is a polypeptide or peptide antigen of H3 virus which currently causes disease or infection and its symptoms, such as seasonal H3 influenza, and which is native to certain geographical locales. In another embodiment, the H3 virus antigen is a polypeptide or peptide antigen which will, in future, cause disease and symptoms of H3 infection. In an embodiment, the H3 virus antigen is a polynucleotide sequence. In an embodiment, the H3 virus antigen is a polynucleotide sequence that encodes a polypeptide or peptide antigen as described herein. By way of example, representative broadly reactive H3 virus HA immunogens are shown in FIGS. 1A-1C.

In another embodiment, the H3 immunogen sequence described herein is expressed in a cell as a polypeptide, protein, or peptide. In an embodiment, the H3 immunogen is isolated and/or purified. In an embodiment, the immunogen is formulated for administration to a subject in need. In an embodiment, the immunogen is administered to a subject in need thereof in an effective amount to elicit an immune response in the subject. In an embodiment, the immune response elicits neutralizing antibodies. In an embodiment, the immune response is prophylactic or therapeutic.

In an embodiment, a non-naturally occurring H3 virus immunogen (immunogen sequence), e.g., a vaccine, is provided that elicits a broadly reactive immune response in a subject following introduction, administration, or delivery of the immunogen to the subject. The route of introduction, administration, or delivery is not limited and may include, for example, intravenous, subcutaneous, intramuscular, oral, etc. routes. The vaccine may be therapeutic (e.g., administered to a subject following a symptom of disease (flu) caused by H3 virus or prophylactic (protective), (e.g., administered to a subject prior to the subject having or expressing a symptom of disease (flu), or full-blown disease, caused by H3 virus).

In an embodiment, the final amino acid sequence of the antigen, e.g., HA, is reverse translated and optimized for expression in mammalian cells. As will be appreciated by the skilled practitioner in the art, optimization of the nucleic acid sequence includes optimization of the codons for expression of a sequence in mammalian cells and RNA optimization (such as RNA stability).

In an embodiment, an isolated nucleic acid molecule (polynucleotide) comprising a nucleotide sequence encoding a polypeptide or peptide antigen, such as an H3 influenza HA polypeptide (or HA1 or HA2 polypeptide), is provided. In certain embodiments, the nucleotide sequence encoding the H3 HA polypeptide is at least 94%, at least 95%, at least 96%, at least 97%, at least 98% or at least 99% identical to a polynucleotide encoding an HA polypeptide (or HA1 or HA2 polypeptide) sequence shown in FIGS. 1A-1C.

In other embodiments, the nucleotide sequence encoding an H3 influenza HA polypeptide (or HA1 or HA2 polypeptide) that is at least 90%, at least 91%, at least 92%, at least 93%, at least 94%, at least 95%, at least 96%, at least 97%, at least 98%, or at least 99% identical to a polynucleotide encoding an H3 HA polypeptide (or HA1 or HA2 polypeptide) sequence shown in FIGS. 1A-1C lacks the start codon encoding an N-terminal methionine.

Vectors containing a nucleotide sequence encoding a non-naturally occurring, broadly reactive polypeptide or peptide antigen, such as an H3 influenza HA polypeptide, (or HA1 or HA2 polypeptide), are provided. In some embodiments, the vectors comprise a nucleotide sequence encoding the polypeptide or peptide antigen, such as an influenza H3 HA polypeptide antigen, that is at least 94%, at least 95%, at least 96%, at least 97%, at least 98% or at least 99% identical to a polynucleotide encoding an H3 HA polypeptide (or HA1 or HA2 polypeptide) sequence shown in FIGS. 1A-1C. In some embodiments, the vector further includes a promoter operably linked to the nucleotide sequence encoding the H3 HA polypeptide (or HA1 or HA2 polypeptide). In a particular embodiment, the promoter is a cytomegalovirus (CMV) promoter. In some embodiments, the nucleotide sequence of the vector is at least 85%, at least 90%, at least 95%, at least 98% or at least 99% identical to a polynucleotide encoding an H3 HA polypeptide (or HA1 or HA2 polypeptide) sequence shown in FIGS. 1A-1C. In particular embodiments, the nucleotide sequence of the vector comprises the polynucleotide encoding an H3 HA polypeptide (or HA1 or HA2 polypeptide) sequence shown in FIGS. 1A-1C. In embodiments, the vector is a prokaryotic or eukaryotic vector. In an embodiment, the vector is an expression vector, such as a eukaryotic (e.g., mammalian) expression vector. In another embodiment, the vector is a plasmid (prokaryotic or bacterial) vector. In another embodiment, the vector is a viral vector.

The vectors used to express an H3 virus antigen, e.g., an H3 viral protein, such as the HA protein, as described herein may be any suitable expression vectors known and used in the art. The vectors can be, for example, mammalian expression vectors or viral vectors. In some embodiments, the vector is the pTR600 expression vector (U.S. Patent Application Publication No. 2002/0106798, herein incorporated by reference; Ross et al., 2000, *Nat Immunol.* 1 (2): 102-103; and Green et al., 2001, *Vaccine* 20:242-248).

Provided are H3 influenza virus-derived, non-naturally occurring polypeptide antigens, e.g., H3 influenza HA polypeptide antigens, or HA1 or HA2 polypeptide antigens, produced by transfecting a host cell with an expression vector as known and used in the art under conditions sufficient to allow for expression of the polypeptide, e.g., an H3 HA, HA1, or HA2 polypeptide, in the cell. Isolated cells containing the vectors are also provided.

Also provided are non-naturally occurring, broadly reactive, pan-epitopic H3 antigen polypeptides as described herein, such as pan-epitopic, broadly reactive H3 influenza HA polypeptides. In certain embodiments, the amino acid sequence of the polypeptide is at least 95% to 99% (inclusive) identical to the amino acid sequence of an HA, HA1, or HA2 polypeptide as shown in FIGS. 1A-1C. In particular embodiments, the amino acid sequence of the H3 influenza HA, HA1, or HA2 polypeptide that is at least 95% to 99% (inclusive) identical to the amino acid sequence of an HA, HA1, or HA2 polypeptide shown in FIGS. 1A-1C lacks the N-terminal methionine residue. In a particular embodiment, the amino acid sequence of the H3 influenza HA polypeptide is at least 95% to 99% (inclusive) identical to amino acids 1-566 of the H3 HA polypeptides shown in FIGS. 1A-1C.

In some embodiments, fusion proteins comprising the broadly reactive, pan-epitopic H3 virus antigen polypeptides described herein, e.g., without limitation, the H3 influenza HA polypeptides disclosed herein, are also provided. In some embodiments, the H3 influenza HA polypeptide can be fused to any heterologous amino acid sequence to form the fusion protein. By way of example, HA1 and HA2 polypeptides may be generated independently and then fused together to produce an H3 HA polypeptide antigen, e.g., comprising 566 amino acids.

Also provided are virus-like particles (VLPs), in particular, H3 influenza VLPs, containing a pan-epitopic, broadly reactive protein antigen, e.g., H3 influenza HA, HA1, or HA2 protein, as described herein. In certain embodiments, the HA protein of the VLP is at least or equal to 94%, at least or equal to 95%, at least or equal to 96%, at least or equal to 97%, at least or equal to 98%, at least or equal to 99% or 100% identical to the H3 HA proteins as shown in FIGS. 1A-1C. The virus or influenza VLPs can further include any additional viral or influenza proteins necessary to form the virus particle. In certain embodiments, the virus or influenza VLPs further include influenza neuraminidase (NA) protein, influenza matrix (M1) protein, or both.

Also provided is an H3 influenza VLP containing an H3 influenza HA, HA1, or HA2 polypeptide as described herein, produced by transfecting a host cell with a vector containing a polynucleotide encoding the H3 HA, HA1, or HA2 polypeptide. Also provided in an embodiment is an H3 influenza VLP containing an H3 influenza HA polypeptide, or HA1 or HA2 polypeptide, as described herein, produced by transfecting a host cell with a vector encoding the H3 HA, HA1, or HA2 polypeptide, a vector encoding an influenza NA protein and a vector encoding an influenza M1 protein, under conditions sufficient to allow for expression of the H3 HA, NA and M1 proteins. Such VLPs comprising the sequences as presented in FIGS. 1A-1C and used as immunogens generate antibodies having high hemagglutinin inhibition (HAI) titers against different strains of H3 influenza virus, as observed in FIGS. 2A-2C.

Collections of plasmids (vectors) are also contemplated. In certain embodiments, the collection of plasmids includes a plasmid encoding an influenza H3 NA, a plasmid encoding an H3 influenza MA, and a plasmid encoding a broadly reactive H3 HA protein as described herein. In some embodiments, the nucleotide sequence encoding an H3 influenza HA protein of the HA-encoding plasmid is at least 94%, at least 95%, at least 96%, at least 97%, at least 98% or at least 99% identical to a polynucleotide encoding an H3 HA amino acid sequence as shown in FIGS. 1A-1C. In some embodiments, the nucleotide sequence encoding a codon-optimized H3 influenza HA protein of the HA-encoding plasmid is at least 94%, at least 95%, at least 96%, at least 97%, at least 98% or at least 99% identical to a polynucleotide encoding an H3 HA amino acid sequence as shown in FIGS. 1A-1C.

In the context of the present disclosure, "broadly reactive" or "broadly active" means that the H3 protein (e.g., an H3 HA protein sequence) is immunogenic and contains a diversity of epitopes (antigenic determinants; pan-epitopic) that elicit in a subject an immune response (e.g., neutralizing antibodies directed against the diversity of H3 virus HA epitopes, frequently accompanied by a T-cell response) sufficient to treat disease or infection, and/or to inhibit, neutralize, or prevent infection, caused by most or all H3 influenza viruses within a specific subtype, or by related virus strains. In embodiments, the broadly reactive, H3 virus-derived antigen protein, e.g., HA protein, is capable of eliciting a protective immune response against most or all known H3 influenza virus isolates, such as about 80%, about 85%, about 90%, about 95%, or about 96%-99% of the known H3 influenza virus isolates.

Compositions and Pharmaceutical Compositions for Administration

Compositions comprising a broadly reactive, pan-epitopic H3 influenza HA protein, or a fusion protein or VLP comprising such a broadly reactive H3 influenza HA protein as described herein are provided. In some embodiments, the compositions further comprise a pharmaceutically acceptable carrier, excipient, or vehicle. In some embodiments, an adjuvant (a pharmacological or immunological agent that modifies or boosts an immune response, e.g. to produce more antibodies that are longer-lasting) is also employed. For example, without limitation, the adjuvant can be an inorganic compound, such as alum, aluminum hydroxide, or aluminum phosphate; mineral or paraffin oil; squalene; detergents such as Quil A; plant saponins; Freund's complete or incomplete adjuvant, a biological adjuvant (e.g., cytokines such as IL-1, IL-2, or IL-12); bacterial products such as killed *Bordetella pertussis*, or toxoids; or immunostimulatory oligonucleotides (such as CpG oligonucleotides).

Compositions and preparations (e.g., physiologically or pharmaceutically acceptable compositions) containing the non-naturally occurring, broadly reactive, pan-epitopic H3 influenza HA polypeptides and H3 influenza virus-like particles (VLPs) for parenteral administration include, without limitation, sterile aqueous or non-aqueous solutions, suspensions, and emulsions. Nonlimiting examples of non-aqueous solvents include propylene glycol, polyethylene glycol, vegetable oils, such as olive oil and canola oil, and injectable organic esters, such as ethyl oleate. Aqueous carriers include water, alcoholic/aqueous solutions, emulsions or suspensions, including saline and buffered media. Parenteral vehicles include, for example, sodium chloride solution, Ringer's dextrose, dextrose and sodium chloride, lactated Ringer's, or fixed oils. Intravenous vehicles include, for example, fluid and nutrient replenishers, electrolyte replenishers (such as those based on Ringer's dextrose), and the like. Preservatives and other additives may also be present in such compositions and preparations, such as, for example, antimicrobials, antioxidants, chelating agents, colorants, stabilizers, inert gases and the like.

Some of the compositions may potentially be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids, such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, tri-alkyl and aryl amines and substituted ethanolamines.

Provided herein are pharmaceutical compositions which include a therapeutically effective amount of a non-naturally occurring, broadly reactive, pan-epitopic, H3 virus protein antigen, or H3 influenza VLPs, alone, or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration.

The composition can also contain minor amounts of wetting or emulsifying agents, or pH buffering agents. The composition can be a liquid or aqueous solution, suspension, emulsion, dispersion, tablet, pill, capsule, powder, or sustained release formulation. A liquid or aqueous composition can be lyophilized and reconstituted with a solution or buffer prior to use. The composition can be formulated as a suppository, with traditional binders and carriers such as triglycerides. Oral formulations can include standard carriers, such as pharmaceutical grades of mannitol, lactose, starch, magnesium stearate, sodium saccharine, cellulose, and magnesium carbonate. Any of the commonly known pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used in the compositions and administration methods as described are normal saline and sesame oil.

Methods of Treatment, Administration and Delivery

Methods of treating a disease or infection, or symptoms thereof, caused by H3 influenza virus are provided. The methods comprise administering a therapeutically effective amount of a broadly reactive, pan-epitopic immunogen as described herein or a pharmaceutical composition comprising the immunogen, or a vaccine (e.g., a VLP vaccine) as described herein to a subject (e.g., a mammal), in particular, a human subject). One embodiment involves a method of treating a subject suffering from, or at risk of or susceptible to disease or infection, or a symptom thereof, caused by H3 influenza virus. The method includes administering to the subject (e.g., a mammalian subject), an amount or a therapeutic amount of an immunogenic composition or a vaccine comprising a non-naturally occurring, broadly reactive, pan-epitopic, H3 virus antigen polypeptide, such as HA polypeptide, or HA polypeptide VLPs, sufficient to treat the disease, infection, or symptoms thereof, caused by H3 influenza virus under conditions in which the disease, infection, and/or the symptoms thereof are treated.

In an embodiment, the methods herein include administering to the subject (including a human subject identified as in need of such treatment) an effective amount of a non-naturally occurring, broadly reactive, pan-epitopic, H3 virus antigen polypeptide, such as H3 virus HA polypeptide, or a vaccine, or a composition as described herein to produce such effect. The treatment methods are suitably administered to subjects, particularly humans, suffering from, having, susceptible to, or at risk of having a disease, disorder, infection, or symptom thereof, namely, flu or influenza. Identifying a subject in need of such treatment can be based on the judgment of the subject or of a health care professional and can be subjective (e.g. opinion) or objective (e.g. measurable by a test or diagnostic method). Briefly, the determination of those subjects who are in need of treatment or who are "at risk" or "susceptible" can be made by any objective or subjective determination by a diagnostic test (e.g., genetic test, enzyme or protein marker assay), marker analysis, family history, and the like, including an opinion of the subject or a health care provider. The non-naturally occurring, broadly reactive, pan-epitopic H3 immunogens, such as H3 HA polypeptide immunogens and vaccines as described herein, may also be used in the treatment of any other disorders in which infection or disease caused by H3 influenza virus may be implicated. A subject undergoing treatment can be a non-human mammal, such as a veterinary subject, or a human subject (also referred to as a "patient").

In addition, prophylactic methods of preventing or protecting against a disease or infection, or symptoms thereof, caused by H3 influenza virus are provided. Such methods comprise administering a therapeutically effective amount of a pharmaceutical composition comprising an H3 immunogenic composition or vaccine (e.g., an H3 VLP vaccine) as described herein to a subject (e.g., a mammal such as a human), in particular, prior to infection of the subject or prior to onset of the disease, such as H3 virus-associated disease.

In another embodiment, a method of monitoring the progress of an H3 virus infection or disease caused by H3 virus, or monitoring treatment of the H3 infection or disease is provided. The method includes determining a level of a diagnostic marker or biomarker (e.g., an H3 virus protein, such as H3 HA), or a diagnostic measurement (e.g., screening assay or detection assay) in a subject suffering from or susceptible to infection, disease or symptoms thereof associated with H3 influenza virus, in which the subject has been administered an amount (e.g., a therapeutic amount) of a non-naturally occurring, broadly reactive, pan-epitopic H3 virus HA protein as described herein, or a vaccine as described herein, sufficient to treat the infection, disease, or symptoms thereof. The level or amount of the marker or biomarker (e.g., protein) determined in the method can be compared to known levels of the marker or biomarker in samples from healthy, normal controls; in a pre-infection or pre-disease sample of the subject; or in other afflicted/infected/diseased patients to establish the treated subject's disease status. For monitoring, a second level or amount of the marker or biomarker in in a sample obtained from the subject is determined at a time point later than the determination of the first level or amount, and the two marker or biomarker levels or amounts can be compared to monitor the course of disease or infection, or the efficacy of the therapy/treatment. In certain embodiments, a pre-treatment level of the marker or biomarker in the subject (e.g., in a sample obtained from the subject) is determined prior to beginning treatment as described; this pre-treatment level of marker or biomarker can then be compared to the level of the marker or biomarker in the subject after the treatment commences and/or during the course of treatment to determine the efficacy of (monitor the efficacy of) the disease treatment.

The non-naturally occurring, broadly reactive, pan-epitopic, H3 virus antigen polypeptides, such as H3 virus HA polypeptides as described, and VLPs comprising H3 HA polypeptides, or compositions thereof, can be administered to a subject by any of the routes normally used for introducing a recombinant protein, composition containing the recombinant protein, or recombinant virus into a subject. Routes and methods of administration include, without limitation, intradermal, intramuscular, intraperitoneal, intrathecal, parenteral, such as intravenous (IV) or subcutaneous (SC), vaginal, rectal, intranasal, inhalation, intraocular, intracranial, or oral. Parenteral administration, such as subcutaneous, intravenous or intramuscular administration, is generally achieved by injection (immunization). Injectables can be prepared in conventional forms and formulations, either as liquid solutions or suspensions, solid forms (e.g., lyophilized forms) suitable for solution or suspension in liquid prior to injection, or as emulsions. Injection solutions and suspensions can be prepared from sterile powders, granules, and tablets. Administration can be systemic or local.

The non-naturally occurring, broadly reactive, pan-epitopic, H3 virus polypeptides, such as H3 virus HA polypeptides as described, and VLPs comprising H3 HA polypeptides, or compositions thereof, can be administered in any suitable manner, such as with pharmaceutically acceptable carriers as described supra. Pharmaceutically acceptable carriers are determined in part by the particular immunogen or composition being administered, as well as by the particular method used to administer the composition.

Accordingly, a pharmaceutical composition comprising the non-naturally occurring, broadly reactive, pan-epitopic, H3 virus antigen polypeptides, such as H3 virus HA polypeptides, and VLPs comprising H3 HA polypeptides, or compositions thereof, can be prepared using a wide variety of suitable and physiologically and pharmaceutically acceptable formulations.

Administration of the broadly reactive, pan-epitopic, H3 virus antigen polypeptides, such as H3 virus HA polypeptides, and VLPs comprising HA polypeptides, or compositions thereof, can be accomplished by single or multiple doses. The dose administered to a subject should be sufficient to induce a beneficial therapeutic response in a subject over time, such as to inhibit, block, reduce, ameliorate, protect against, or prevent disease or infection by H3 influenza virus. The dose required will vary from subject to subject depending on the species, age, weight and general condition of the subject, by the severity of the infection being treated, by the particular composition being used and by the mode of administration. An appropriate dose can be determined by a person skilled in the art, such as a clinician or medical practitioner, using only routine experimentation.

Further provided is a method of eliciting an immune response to H3 influenza virus in a subject by administering to the subject a non-naturally occurring, broadly reactive, pan-epitopic, H3 influenza HA protein disclosed herein, fusion proteins containing the H3 influenza HA protein, VLPs containing the influenza HA protein, or compositions thereof as described herein. In some embodiments, the H3 HA protein, HA fusion protein or VLP can be administered using any suitable route of administration, such as, for example, by intramuscular injection. In some embodiments, the H3 HA protein, fusion protein, or VLP is administered as a composition comprising a pharmaceutically acceptable carrier. In some embodiments the composition comprises an adjuvant selected from, for example, alum, Freund's complete or incomplete adjuvant, a biological adjuvant or immunostimulatory oligonucleotides (such as CpG oligonucleotides). In other embodiments, the composition may be administered in combination with another therapeutic agent or molecule.

Also provided is a method of immunizing a subject against infection or disease or the symptoms thereof caused by the H3 influenza virus, in which the method involves administering to the subject VLPs containing a non-naturally occurring, pan-epitopic, broadly reactive H3 influenza HA protein as described herein, or administering an immunogenic composition thereof. In some embodiments of the method, the composition further comprises a pharmaceutically acceptable carrier and/or an adjuvant. For example, the adjuvant can be alum, Freund's complete or incomplete adjuvant, a biological adjuvant or immunostimulatory oligonucleotides (such as CpG oligonucleotides). In an embodiment, the H3 VLPs (or compositions thereof) are administered intramuscularly.

In some embodiments of the methods of eliciting an immune response or immunizing a subject against virus infection or disease caused by or associated with H3 influenza virus, the subject is administered at least 1 μg of the VLPs containing a non-naturally occurring, broadly reactive, pan-epitopic H3 virus HA protein, such as at least 5 μg, at least 10 μg, at least 15 μg, at least 20 μg, at least 25 μg, at least 30 μg, at least 40 μg g or at least 50 μg of the VLPs containing the non-naturally occurring, broadly reactive, pan-epitopic H3 virus HA protein, for example about 1 to about 50 μg or about 1 to about 25 μg of the VLPs containing the H3 HA protein. In particular examples, the subject is administered about 5 to about 20 μg of the VLPs, or about 10 to about 15 μg of the VLPs. In a specific, yet nonlimiting example, the subject is administered about 15 μg of the VLPs. However, one of skill in the art is capable of determining a therapeutically effective amount of VLPs (for example, an amount that provides a therapeutic effect or protection against H3 influenza virus infection) suitable for administering to a subject in need of treatment or protection from virus infection.

It is expected that the administration of VLPs comprising a non-naturally occurring, broadly reactive, pan-epitopic H3 HA protein as described herein will elicit high titers of neutralizing antibodies directed against the diverse repertoire of epitopic determinants on the H3 HA protein immunogen, as well as protective levels of H3 HA-inhibiting (HAI) antibodies that are directed against a number of representative H3 isolates and will provide complete protection against lethal challenge with H3 virus and/or related H3 virus types. The VLPs containing a non-naturally occurring, broadly reactive, pan-epitopic H3 influenza HA protein as described herein elicit a broader immune response (e.g., elicit neutralizing antibodies directed against a broader range of H3 virus isolates compared to the immune response elicited by a polyvalent H3 influenza virus vaccine.

Adjuvants and Combination Therapies

The H3 virus immunogens or immunogenic compositions containing an H3 protein antigen (e.g., an H3 HA antigen), or containing H3 virus VLPs as described herein, can be administered alone or in combination with other therapeutic agents to enhance antigenicity or immunogenicity, i.e., to increase an immune response, such as the elicitation of specific antibodies, in a subject. For example, the H3 influenza VLPs can be administered with an adjuvant, such as alum, Freund's incomplete adjuvant, Freund's complete adjuvant, biological adjuvant, or immunostimulatory oligonucleotides (such as CpG oligonucleotides).

One or more cytokines, such as interleukin-1 (IL-2), interleukin-6 (IL-6), interleukin-12 (IL-12), the protein memory T-cell attractant "Regulated on Activation, Normal T Expressed and Secreted" (RANTES), granulocyte-macrophage-colony stimulating factor (GM-CSF), tumor necrosis factor-alpha (TNF-α), or interferon-gamma (IFN-γ); one or more growth factors, such as GM-CSF or granulocyte-colony stimulation factor (G-CSF); one or more molecules such as the TNF ligand superfamily member 4 ligand (OX40L) or the type 2 transmembrane glycoprotein receptor belonging to the TNF superfamily (4-1BBL), or combinations of these molecules, can be used as biological adjuvants, if desired or warranted (see, e.g., Salgaller et al., 1998, *J. Surg. Oncol.* 68 (2): 122-38; Lotze et al., 2000, *Cancer J. Sci. Am.* 6 (Suppl 1): S61-6; Cao et al., 1998, *Stem Cells* 16 (Suppl 1): 251-60; Kuiper et al., 2000, *Adv. Exp. Med. Biol.* 465:381-90). These molecules can be administered systemically (or locally) to a subject.

Several ways of inducing cellular responses, both in vitro and in vivo, are known and practiced in the art. Lipids have been identified as agents capable of assisting in priming cytotoxic lymphocytes (CTL) in vivo against various antigens. For example, palmitic acid residues can be attached to the alpha and epsilon amino groups of a lysine residue and then linked (for example, via one or more linking residues, such as glycine, glycine-glycine, serine, serine-serine, or the like) to an immunogenic peptide (U.S. Pat. No. 5,662,907). The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor-specific CTL when covalently attached to an appropriate peptide (see, e.g., Deres et al., 1989, *Nature* 342:561). Moreover, the induction of neutralizing antibodies can also be primed with the same molecule conjugated to a peptide which displays an appropriate epitope, and two compositions can be combined to elicit both humoral and cell-mediated responses where such a combination is deemed desirable.

While treatment methods may involve the administration of VLPs containing a non-naturally occurring, broadly reactive, pan-epitopic H3 HA immunogenic protein as described herein, one skilled in the art will appreciate that the non-naturally occurring, broadly reactive, pan-epitopic H3 influenza HA protein itself (in the absence of a viral particle), as a component of a pharmaceutically acceptable composition, or as a fusion protein, can be administered to a subject in need thereof to elicit an immune response in the subject.

Kits

Also provided are kits containing a non-naturally occurring, broadly reactive, pan-epitopic H3 virus immunogen as described, or a vaccine, or a pharmaceutically acceptable composition containing the immunogen and a pharmaceutically acceptable carrier, diluent, or excipient, for administering to a subject, for example. The immunogen may be in the form of an H3 virus protein (polypeptide) or a polynucleotide (a polynucleotide encoding an H3 virus polypeptide, e.g., an H3 HA protein), as described herein. Kits containing one or more of the plasmids, or a collection of plasmids as described herein, are also provided. As will be appreciated by the skilled practitioner in the art, such a kit may contain one or more containers that house the immunogen, vaccine, or composition, diluents or excipients, as necessary, and instructions for use.

Recombinant Polypeptide Expression

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, May be considered in making and practicing the invention. Particularly useful techniques for particular embodiments will be discussed in the sections that follow.

EXAMPLES

The following examples are provided to illustrate particular features and/or embodiments. The examples should not be construed to limit the disclosure to the particular features or embodiments described.

Example 1

Hemagglutination-Inhibition (HAI) Assay

A hemagglutination inhibition (HAI) assay was used to assess functional antibodies to the HA protein that are able to inhibit agglutination of guinea pig, horse, or turkey erythrocytes (red blood cells (RBCs)).

Sera used in the assay contained antibodies generated following immunization of animals (mice) with VLPs containing H3 virus HA antigen sequences such as described herein, e.g., TJ2, TJ-3, TJ5-9 (FIGS. 1A-1C), other H3 virus HA sequences (e.g., Bris/07, Perth/09, Vic/11, Tx/12, Switz/13, HK/14), wild-type H3 HA sequences, and/or PBS control. For immunization, 5 mice were used per group. Each animal received 3 µg of the HA antigen/VLP and squalene adjuvant (AF03) (MF Klucker, 2012, J. Pharm. Sci., 101 (12): 4490-4500) per dose. A homologous prime, boost, boost immunization/administration regimen was employed. Mice were bled on day 77 following a boost with the immunogen on day 56, as presented in Table 1 below.

TABLE 1

| Aug. 18, 2017 Prime D0 | Sep. 15, 2017 Boost D28 | Sep. 29, 2017 Bleed D42 | Oct. 13, 2017 Boost D56 | Oct. 27, 2017 Bleed D70 | Nov. 2, 2017 Bleed D77 |
|---|---|---|---|---|---|
| TJ-2 | TJ-2 | | TJ-2 | | |
| TI-3 | TJ-3 | | TJ-3 | | |
| TJ-5 | TJ-5 | | TJ-5 | | |
| TJ-6 | TJ-6 | | TJ-6 | | |
| TJ-7 | TJ-7 | | TJ-7 | | |
| TJ-8 | TJ-8 | | TJ-8 | | |
| TJ-9 | TJ-9 | | TJ-9 | | |
| Bris/07 | Bris/07 | | Bris/07 | | |
| Perth/09 | Perth/09 | | Perth/09 | | |
| Vic/11 | Vic/11 | | Vic/11 | | |
| Tx/12 | Tx/12 | | Tx/12 | | |
| Switz/13 | Switz/13 | | Switz/13 | | |
| HK/14 | HK/14 | | HK/14 | | |

The protocols were adapted from the WHO laboratory influenza surveillance manual (Gillim-Ross and Subbarao, 2006, Clin Microbiol Rev 19 (4): 614-636) and use the host-species that is frequently used to characterize contemporary H3N2 strains that have preferential binding to alpha (2, 6) linked sialic acid receptors. Turkey or guinea pig erythrocytes were used to compare whether there was a difference in HAI depending on the type of erythrocyte that was used.

To inactivate nonspecific inhibitors, sera were treated with receptor-destroying enzyme (RDE) (Denka Seiken, Co., Japan) prior to being tested. (Bright et al., 2005, Lancet 366 (9492): 1175-1181; Bright et al., 2003, Virology 308 (2): 270-278; Bright et al., 2006, JAMA 295 (8): 891-894; Mitchell et al., 2004, Vaccine 21 (9-10): 902-914; Ross et al., 2000, Nat Immunol 1 (2): 127-131). Briefly, three parts of RDE was added to one part of sera and incubated overnight at 37° C. RDE was inactivated by incubation at 56° C. for approximately 30 minutes (~30 min.). RDE-treated sera were diluted in a series of two-fold serial dilutions in v-bottom microtiter plates. An equal volume of each virus, e.g., H3N2 virus, adjusted to approximately 8 hemagglutination units (HAU)/50 µl, was added to each well. The plates were covered and incubated at room temperature for 20 minutes, followed by the addition of 0.75% or 0.8% guinea pig erythrocytes (Lampire Biologicals, Pipersville, PA, USA) in phosphate buffered saline (PBS). Red blood cells (erythrocytes) were stored at 4° C. and used within 72 hours of preparation.

The plates were mixed by agitation and covered, and the RBCs were allowed to settle for 1 hour at room temperature. The HAI titer was determined by the reciprocal dilution of the last well that contained non-agglutinated RBCs. Positive and negative serum controls were included for each plate. All mice were negative (HAI≤1:10) for preexisting antibodies to currently circulating human influenza viruses prior to vaccination. Seroprotection was defined as HAI titer >1:40, and seroconversion was defined as a 4-fold increase in titer compared to baseline, as per the WHO and European Committee for Medicinal Products to evaluate influenza vaccines. A more stringent threshold of >1:80 was often examined. Because mice are naïve and seronegative at the time of vaccination, seroconversion and seroprotection rates are interchangeable in the experiments.

Figure 2B:
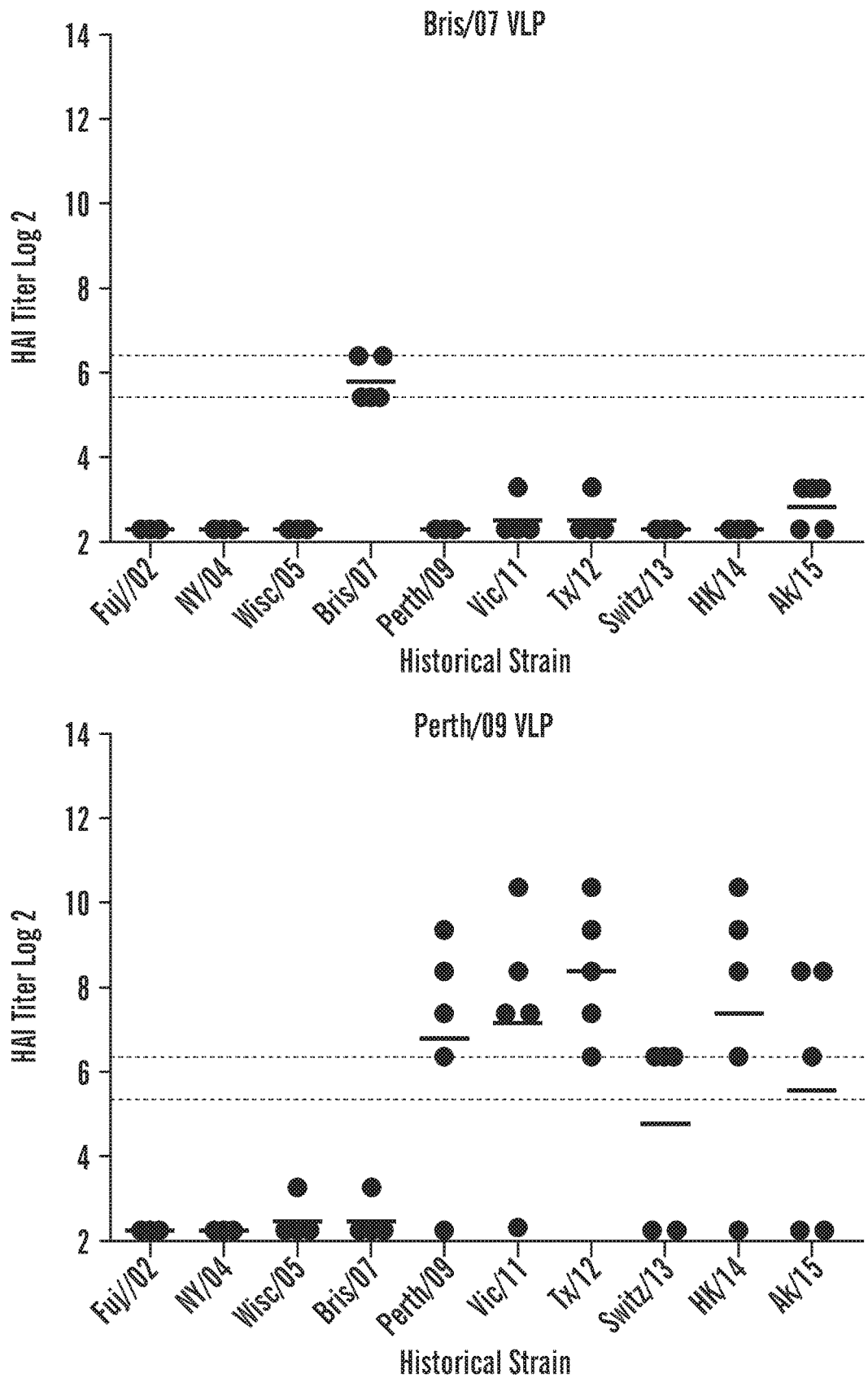
Figure 2B:
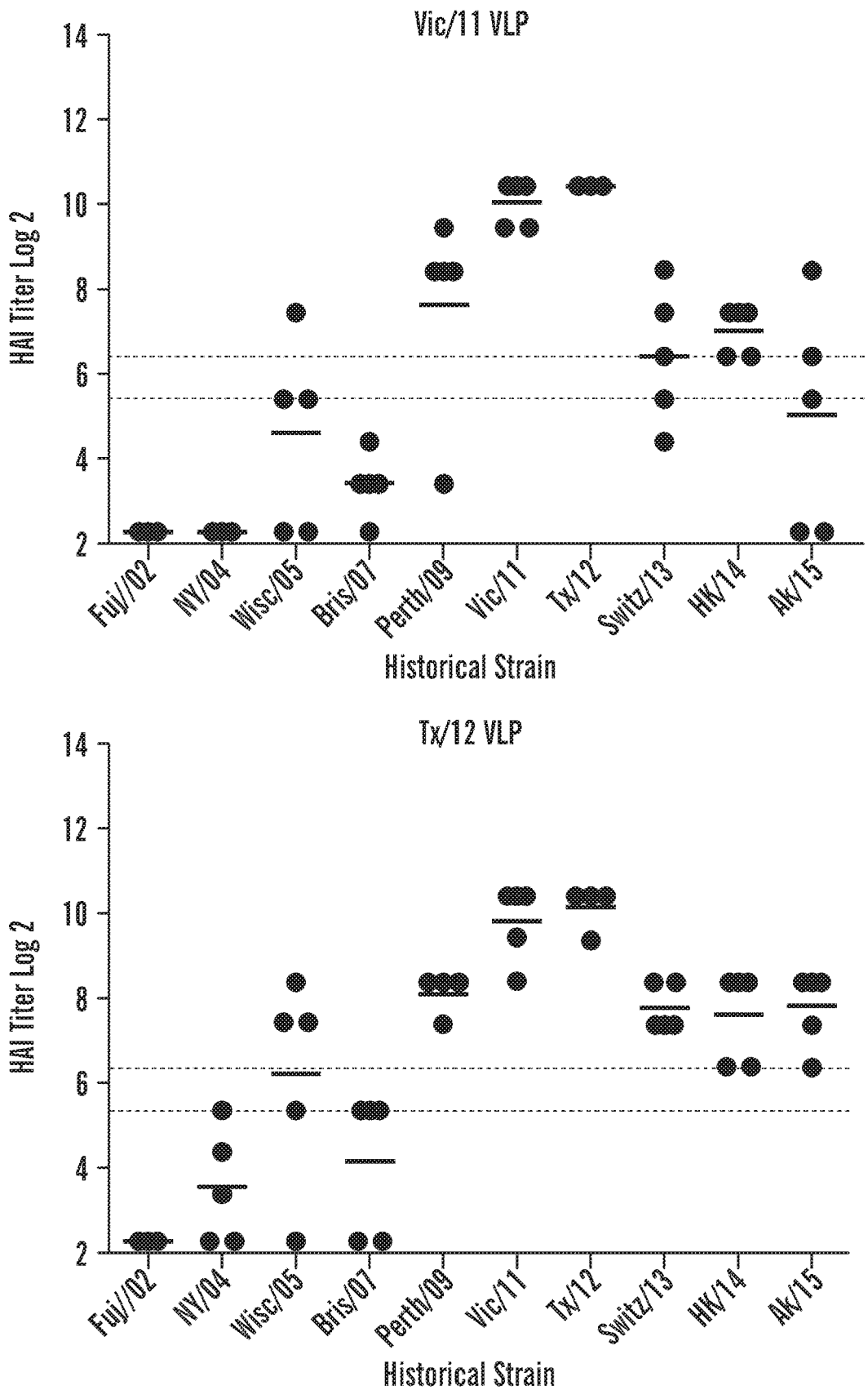
Figure 2B:
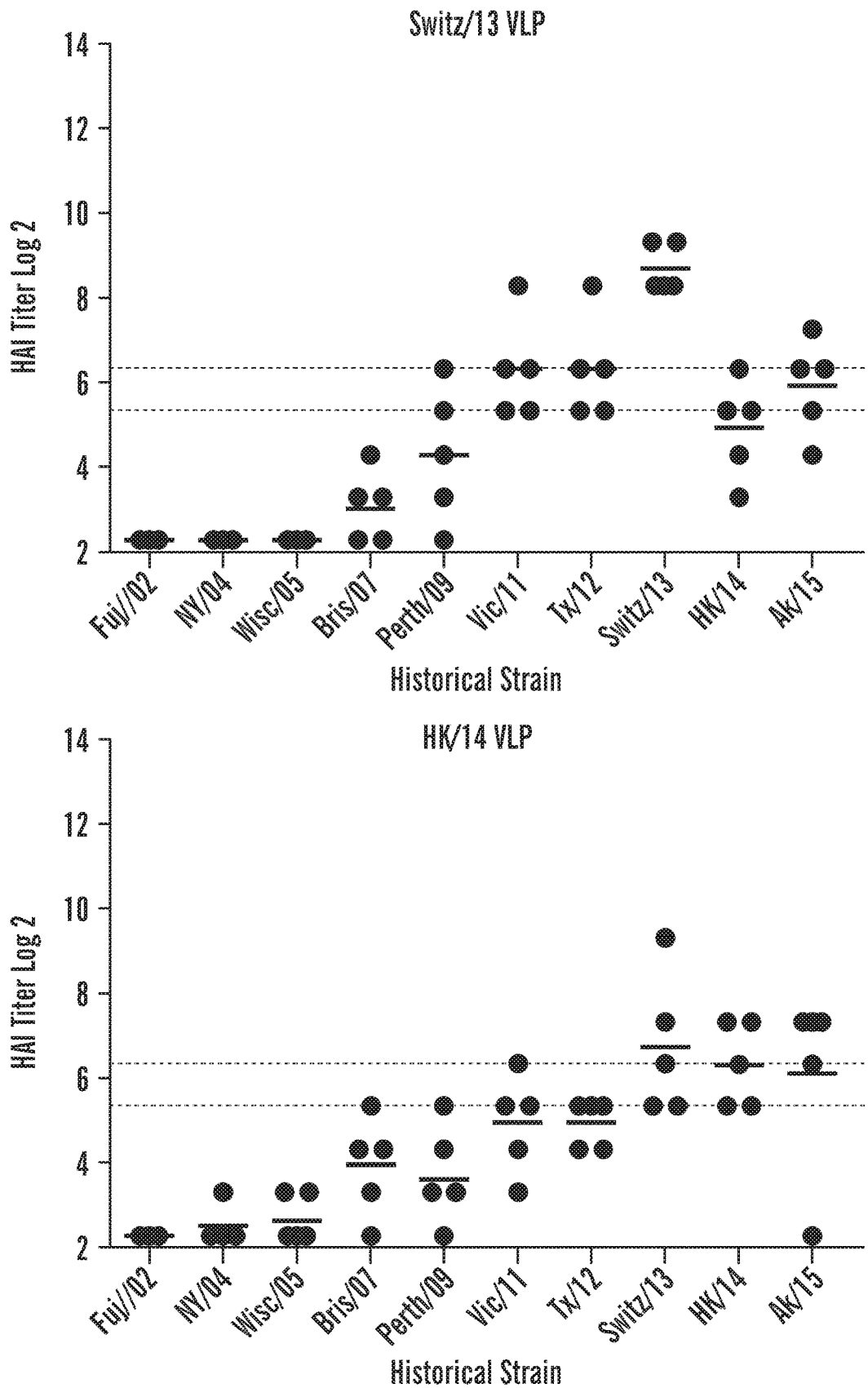
Figure 2C:
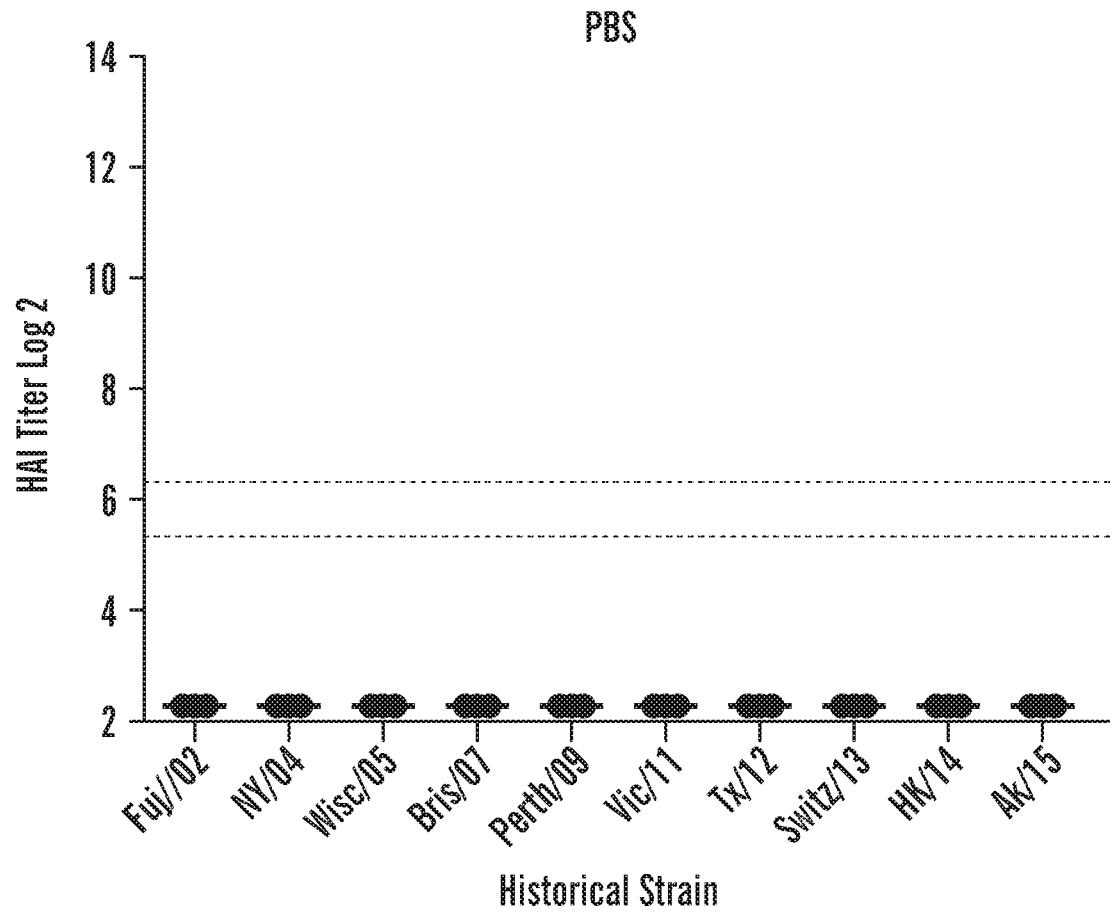

FIGS. 2A-2C show hemagglutination inhibition antibody titers of antibodies generated against VLPs comprising the H3 virus HA immunogens (immunogen sequences) using the immunization/administration regimen as described above and herein (FIG. 2A), compared with VLPs produced using different H3 virus HA sequences (FIG. 2B) or PBS (FIG. 2C).

Example 2

Virus-Like Particle (Vaccine) Preparation

Mammalian 293T cells were transfected with each of three mammalian expression plasmids expressing either the influenza neuraminidase (A/mallard/Alberta/24/01, H7N3), the HIV p55 Gag sequences, or one of the broadly reactive HA expression plasmids (e.g., containing sequence encoding the HA immunogens shown in FIGS. 1A-1C), using previously described methods (see, e.g., US Patent Application Publication US 2015/0030628). Following 72 hours of incubation at 37° C., supernatants from transiently transfected cells were collected, centrifuged to remove cellular debris, and filtered through a 0.22 μm pore membrane. Mammalian virus-like particles (VLPs) were purified and sedimented by ultracentrifugation on a 20% glycerol cushion at 135,000×g for 4 hours at 4° C. VLPs were resuspended in phosphate buffered saline (PBS) and total protein concentration was assessed using a conventional bicinchoninic acid assay (BCA). The hemagglutination activity of each preparation of VLPs was determined by adding an equal volume of turkey or guinea pig red blood cells (RBCs) to a V-bottom 96-well plate and incubating with serially diluted volumes of VLPs for a 30-minute incubation at room temperature (RT). The highest dilution of VLP with full agglutination of RBCs was considered the endpoint HA titer.

Example 3

Determination of HA Content by Enzyme Linked Immunosorbent Assay (ELISA)

A high-affinity, 96-well, flat-bottom ELISA plate was coated with 5-10 μg of total protein of VLP and serial dilutions of a recombinant H3 antigen (3006_H3_Vc, Protein Sciences, Meriden, CT) in ELISA carbonate buffer (50 mM carbonate buffer, pH 9.5) were added to the wells. The plate was incubated overnight at 4° C. on a rocker. The next morning, the plates were washed in PBS with 0.05% Tween-20 (PBST), and non-specific epitopes were blocked with 1% bovine serum albumin (BSA) in PBST solution for 1 hour at RT. The buffer was removed, and stalk-specific Group 2 antibody CR8020 (Tharakaraman, K. et al., 2014, *Cell Host & Microbe*, Vol. 15, pp. 644-651; Ekiert, D. C. et al., 2012, *Science*, 333 (6044): 843-850; Creative Biolabs, Shirley, NY) was added to plate, followed by a 1 hour incubation at 37° C. The plates were washed and then were probed with goat anti-human IgG horseradish-peroxidase-conjugated secondary antibody (2040-05, Southern Biotech, Birmingham, AL) for 1 hour at 37° C.

The plates were washed. Freshly prepared o-phenylenediamine dihydrochloride (OPD) (P8287, Sigma, City, State, USA) substrate in citrate buffer (P4922, Sigma) was then added to wells, followed by the addition of 1N $H_2SO_4$ stopping reagent. The plates were read at 492 nm absorbance using a microplate reader (Powerwave XS, Biotek, Winooski, VT). Background signal was subtracted from negative wells. Linear regression standard curve analysis was performed using the known concentrations of recombinant standard antigen to estimate the HA content in lots of VLPs.

Example 4

Mouse and Ferret Studies
Mouse Studies

BALB/c mice (*Mus musculus*, females, 6 to 8 weeks of age) were purchased from Jackson Laboratory (Bar Harbor, ME, USA), housed in microisolator units and allowed free access to food and water. The animals were cared for under University of Georgia Research Animal Resources guidelines for laboratory animals. All procedures were reviewed and approved by the Institutional Animal Care and Use Committee (IACUC). Mice (5 mice per group) were vaccinated with purified virus-like particles (VLPs), (3.0 μg/mouse), based upon HA content from the ELISA quantification, and VLP immunogens (vaccines) were delivered to the animals via intramuscular injection at week 0. Animals were boosted with the same immunogen (vaccine) at the same dose at weeks 4 and 8. Vaccines at each dose were formulated with an emulsified squalene-in-water adjuvant (Sanofi Pasteur, Lyon, France). The final concentration after mixing 1:1 with VLPs was 2.5% squalene. Twenty-eight days after each vaccination, blood samples were collected via the submandibular cheek, and the samples were transferred to a microcentrifuge tube. The tubes were centrifuged at 10,000 rpm for 10 minutes. Serum samples were removed and frozen at −20° C.±5° C.

Ferret Studies

Fitch ferrets (*Mustela putorius faro*, female, 6-12-months of age), influenza naive and de-scented, were purchased from Marshall Farms (Sayre, Pa., USA). Ferrets were pair-housed in stainless steel cages (Shor-line, Kansas City, Kans., USA) containing Sani-chips Laboratory Animal Bedding (P.J. Murphy Forest Products, Montville, N.J., USA). Ferrets were provided with Teklad Global Ferret Diet (Harlan Teklad, Madison, Wis., USA) and fresh water ad libitum.

The purified VLPs were diluted in PBS, pH 7.2, to achieve final concentration. Ferrets (n=3) were vaccinated with 15 μg of purified VLPs, based upon HA content as determined by densitometry assay, via intramuscular injection in the quadriceps muscle in a volume of 0.25 ml at week 0, and then were boosted with the same dose at week 3. Vaccines were stored at −80° C. prior to use and formulated with IMJECT® alum adjuvant (IMJECT® Alum; Pierce Biotechnology, Rockford, IL USA) or with the above-described emulsified squalene-in-water adjuvant immediately prior to use. Animals were monitored for adverse events including weight loss, temperature, loss of activity, nasal discharge, sneezing and diarrhea weekly during the vaccination regimen. Prior to vaccination, animals were confirmed by HAI assay to be seronegative for circulating influenza A (e.g., H1N1) and influenza B viruses. Fourteen to twenty-one days after each vaccination, blood was collected from anesthetized ferrets via the anterior vena cava and transferred to a microfuge tube. The tubes were centrifuged; serum was removed and frozen at −20±5° C.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An immunogenic vaccine composition comprising an isolated, recombinantly-produced, non-naturally occurring, broadly reactive antigen of H3 influenza virus (H3 virus) that generates an immune response comprising inhibitory hemagglutinin (HA) antibodies against present and future H3 virus strains; wherein the recombinantly-produced H3 virus antigen comprises an amino acid sequence as set forth in any one of SEQ ID NOs: 3, 6, 10, or 11, and a physiologically acceptable carrier, excipient, or vehicle.

2. The immunogenic vaccine composition comprising the isolated, recombinantly-produced H3 virus antigen of claim 1, wherein the antigen is hemagglutinin (HA) antigen.

3. The immunogenic vaccine composition comprising the isolated, recombinantly-produced H3 virus antigen of claim 1, wherein the antigen consists of an amino acid sequence as set forth in any one of SEQ ID NOs: 3, 6, 10, or 11.

4. The immunogenic vaccine composition comprising the isolated, recombinant H3 virus antigen of claim 1, in the form of a virus-like particle (VLP).

5. The immunogenic vaccine composition comprising the isolated, recombinant H3 virus antigen of claim 1, wherein the immune response comprises the production of neutralizing antibodies.

6. The immunogenic vaccine composition comprising the isolated, recombinant H3 virus antigen of claim 1, wherein the immune response further comprises the production of T-lymphocytes.

7. A pharmaceutically acceptable composition comprising the immunogenic vaccine composition of claim 1.

8. A method of generating an immune response in a subject, the method comprising administering to the subject an effective amount of the immunogenic vaccine composition of claim 1.

9. A method of generating an immune response in a subject, the method comprising administering to the subject an effective amount of the pharmaceutical composition of claim 7.

10. The method of claim 8, wherein the immune response comprises the production of neutralizing antibodies.

11. The method of claim 10, wherein the immune response further comprises the production of T-lymphocytes.

12. The method of claim 8, wherein an adjuvant is concomitantly administered to the subject.

13. A polynucleotide encoding the isolated, recombinant H3 virus antigen of the immunogenic vaccine composition of claim 1.

14. A pharmaceutical composition comprising the polynucleotide of claim 13 and a pharmaceutically acceptable carrier, diluent, or excipient.

15. The polynucleotide of claim 13, which is RNA or DNA.

16. A pharmaceutical composition comprising the polynucleotide of claim 15, and a pharmaceutically acceptable carrier, diluent, or excipient.

17. The immunogenic vaccine composition of claim 1, wherein the isolated, recombinantly-produced H3 virus antigen generates sero-protection in subjects seronegative for circulating influenza A and B viruses prior to vaccination.

18. The immunogenic vaccine composition comprising the isolated, recombinantly-produced H3 virus antigen of claim 1, wherein the immune response comprises inhibitory antibodies or a binding portion thereof directed against one or more of the HA, HA1, or HA2 H3 virus antigens.

* * * * *

SEQUENCE LISTING

```
<160> NUMBER OF SEQ ID NOS: 11

<210> SEQ ID NO 1
<211> LENGTH: 565
<212> TYPE: PRT
<213> ORGANISM: Influenza A virus

<400> SEQUENCE: 1

Met Lys Thr Ile Ile Ala Leu Ser Tyr Ile Phe Cys Leu Ala Leu Gly
```

```
1               5                    10                   15
Gln Asp Leu Pro Gly Asn Asp Asn Ser Thr Ala Thr Leu Cys Leu Gly
                20                   25                   30
His His Ala Val Pro Asn Gly Thr Leu Val Lys Thr Ile Thr Asp Asp
                35                   40                   45
Gln Ile Glu Val Thr Asn Ala Thr Glu Leu Val Gln Ser Ser Ser Thr
50                   55                   60
Gly Lys Ile Cys Asn Asn Pro His Arg Ile Leu Asp Gly Ile Asp Cys
65                   70                   75                   80
Thr Leu Ile Asp Ala Leu Leu Gly Asp Pro His Cys Asp Val Phe Gln
                85                   90                   95
Asn Glu Thr Trp Asp Leu Phe Val Glu Arg Ser Lys Ala Phe Ser Asn
                100                  105                  110
Cys Tyr Pro Tyr Asp Val Pro Asp Tyr Ala Ser Leu Arg Ser Leu Val
                115                  120                  125
Ala Ser Ser Gly Thr Leu Glu Phe Ile Thr Glu Gly Phe Thr Trp Thr
                130                  135                  140
Gly Val Thr Gln Asn Gly Gly Ser Asn Ala Cys Lys Arg Gly Pro Gly
145                  150                  155                  160
Ser Gly Phe Phe Ser Arg Leu Asn Trp Leu Thr Lys Ser Gly Ser Thr
                165                  170                  175
Tyr Pro Val Leu Asn Val Thr Met Pro Asn Asn Asp Asn Phe Asp Lys
                180                  185                  190
Leu Tyr Ile Trp Gly Val His His Pro Ser Thr Asn Gln Glu Gln Thr
                195                  200                  205
Ser Leu Tyr Val Gln Ala Ser Gly Arg Val Thr Val Ser Thr Arg Arg
                210                  215                  220
Ser Gln Gln Thr Ile Ile Pro Asn Ile Gly Ser Arg Pro Trp Val Arg
225                  230                  235                  240
Gly Leu Ser Ser Arg Ile Ser Ile Tyr Trp Thr Ile Val Lys Pro Gly
                245                  250                  255
Asp Val Leu Val Ile Asn Ser Asn Gly Asn Leu Ile Ala Pro Arg Gly
                260                  265                  270
Tyr Phe Lys Met Arg Thr Gly Lys Ser Ser Ile Met Arg Ser Asp Ala
                275                  280                  285
Pro Ile Thr Cys Ile Ser Glu Cys Ile Thr Pro Asn Gly Ser Ile Pro
                290                  295                  300
Asn Asp Lys Pro Phe Gln Asn Val Asn Lys Ile Thr Tyr Gly Ala Cys
305                  310                  315                  320
Pro Lys Tyr Val Lys Gln Asn Thr Leu Lys Leu Ala Thr Gly Met Arg
                325                  330                  335
Asn Val Pro Glu Lys Gln Thr Arg Gly Leu Phe Gly Ala Ile Ala Gly
                340                  345                  350
Phe Ile Glu Asn Gly Trp Glu Gly Met Ile Asp Gly Trp Tyr Gly Phe
                355                  360                  365
Arg His Gln Asn Ser Glu Gly Thr Gly Gln Ala Ala Asp Leu Lys Ser
                370                  375                  380
Thr Gln Ala Ala Ile Asp Gln Ile Asn Gly Lys Leu Asn Arg Val Ile
385                  390                  395                  400
Glu Lys Thr Asn Glu Lys Phe His Gln Ile Glu Lys Glu Phe Ser Glu
                405                  410                  415
Val Glu Gly Arg Ile Gln Asp Leu Glu Lys Tyr Val Glu Asp Thr Lys
                420                  425                  430
```

```
Ile Asp Leu Trp Ser Tyr Asn Ala Glu Leu Leu Val Ala Leu Glu Asn
        435                 440                 445

Gln His Thr Ile Asp Leu Thr Asp Ser Glu Met Asn Lys Leu Phe Glu
    450                 455                 460

Lys Thr Arg Arg Gln Leu Arg Glu Asn Ala Glu Asp Met Gly Asn Gly
465                 470                 475                 480

Cys Phe Lys Ile Tyr His Lys Cys Asp Asn Ala Cys Ile Glu Ser Ile
                485                 490                 495

Arg Asn Gly Thr Tyr Asp His Asp Val Tyr Arg Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Leu Cys Val
    530                 535                 540

Val Leu Leu Gly Phe Ile Met Trp Ala Cys Gln Arg Gly Asn Ile Arg
545                 550                 555                 560

Cys Asn Ile Cys Ile
                565

<210> SEQ ID NO 2
<211> LENGTH: 1720
<212> TYPE: DNA
<213> ORGANISM: Influenza A virus

<400> SEQUENCE: 2
attaatcatg aagaccatca ttgctttgag ctacattttc tgtctggctc tcggccaaga     60
ccttccagga aatgacaaca gcacagcaac gctgtgcctg ggacatcatg cggtgccaaa    120
cggaacacta gtgaaaacaa tcacagatga tcagattgaa gtgactaatg ctactgagct    180
agttcagagc tcctcaacgg ggaaaatatg caacaatcct catcgaatcc ttgatggaat    240
agactgcaca ctgatagatg ctctattggg ggaccctcat tgtgatgttt ttcaaaatga    300
gacatgggac cttttcgttg aacgcagcaa agctttcagc aactgttacc cttatgatgt    360
gccagattat gcctccctta ggtcactagt tgcctcgtca ggcactctgg agtttatcac    420
tgagggtttc acttggactg gggtcactca gaatgggga agcaatgctt gcaaaagggg    480
acctggtagc ggtttttca gtagactgaa ctggttgacc aaatcaggaa gcacatatcc    540
agtgctgaac gtgactatgc caaacaatga caattttgac aaactataca tttgggggt    600 tcaccacccg agcacgaacc aagaacaaac cagcctgtat gttcaagcat cagggagagt    660
cacagtctct accaggagaa gccagcaaac tataatcccg aatatcgggt ccagaccctg    720
ggtaaggggt ctgtctagta gaataagcat ctattggaca atagttaagc cgggagacgt    780
actggtaatt aatagtaatg ggaacctaat cgctcctcgg ggttatttca aaatgcgcac    840
tgggaaaagc tcaataatga ggtcagatgc acctattgat acctgtattt ctgaatgcat    900
cactccaaat ggaagcattc ccaatgacaa gccctttcaa aacgtaaaca agatcacata    960
tggagcatgc cccaagtatg ttaagcaaaa caccctgaag ttggcaacag ggatgcggaa   1020
tgtaccagag aaacaaacta gaggcctatt cggcgcaata gcaggtttca tagaaaatgg   1080
ttgggaggga atgatagacg gttggtacgg tttcaggcat caaaattctg agggcacagg   1140
acaagcagca gatcttaaaa gcactcaagc agccatcgac caaatcaatg ggaaattgaa   1200
cagggtaatc gagaagacga acgagaaatt ccatcaaatc gaaaaggaat tctcagaagt   1260
agaagggaga attcaggacc tcgagaaata cgttgaagac actaaaatag atctctggtc   1320

```
ttacaatgcg gagcttcttg tcgctctgga gaatcaacat acaattgacc tgactgactc    1380
ggaaatgaac aagctgtttg aaaaaacaag gaggcaactg agggaaaatg ctgaagacat    1440
gggcaatggt tgcttcaaaa tataccacaa atgtgacaac gcttgcatag agtcaatcag    1500
aaatgggact tatgaccatg atgtatacag agacgaagca ttaaacaacc ggtttcagat    1560
caaaggtgtt gaactgaagt ctggatacaa agactggatc ctgtggattt cctttgccat    1620
atcatgcttt ttgctttgtg ttgttttgct ggggttcatc atgtgggcct gccagagagg    1680
caacattagg tgcaacattt gcatttgagt gtattagtaa                          1720
```

<210> SEQ ID NO 3
<211> LENGTH: 566
<212> TYPE: PRT
<213> ORGANISM: Influenza A virus

<400> SEQUENCE: 3

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Lys Ser Phe Phe Ser Arg Leu Asn Trp Leu Thr His Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Ser Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asp Val Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300
```

```
Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 4
<211> LENGTH: 566
<212> TYPE: PRT
<213> ORGANISM: Influenza A virus

<400> SEQUENCE: 4

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
```

```
            100                 105                 110
Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
        130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Glu Lys Phe Asp Lys
            180                 185                 190

Leu Tyr Ile Trp Gly Val His His Pro Gly Thr Asp Asn Asp Gln Ile
        195                 200                 205

Ser Leu Tyr Ala Gln Ala Ser Gly Arg Ile Thr Val Ser Thr Lys Arg
        210                 215                 220

Ser Gln Gln Thr Val Ile Pro Asn Ile Gly Ser Arg Pro Arg Val Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
        290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
        370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
        450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525
```

-continued

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 5
<211> LENGTH: 566
<212> TYPE: PRT
<213> ORGANISM: Influenza A virus

<400> SEQUENCE: 5

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met

```
                        325                 330                 335
Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 6
<211> LENGTH: 566
<212> TYPE: PRT
<213> ORGANISM: Influenza A virus

<400> SEQUENCE: 6

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125
```

```
Ala Ser Ser Gly Thr Leu Glu Phe Asn Asn Glu Ser Phe Asn Trp Thr
    130                 135                 140
Gly Val Thr Gln Asn Gly Thr Ser Ser Ala Cys Lys Arg Arg Ser Asn
145                 150                 155                 160
Lys Ser Phe Phe Ser Arg Leu Asn Trp Leu Thr His Leu Lys Phe Lys
                165                 170                 175
Tyr Pro Ala Leu Asn Val Thr Met Pro Asn Asn Glu Lys Phe Asp Lys
            180                 185                 190
Leu Tyr Ile Trp Gly Val His His Pro Gly Thr Asp Asn Asp Gln Ile
        195                 200                 205
Ser Leu Tyr Ala Gln Ala Ser Gly Arg Ile Thr Val Ser Thr Lys Arg
    210                 215                 220
Ser Gln Gln Thr Val Ile Pro Asn Ile Gly Ser Arg Pro Arg Val Arg
225                 230                 235                 240
Asp Val Pro Ser Arg Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
            260                 265                 270
Tyr Phe Lys Ile Arg Ser Gly Lys Ser Ser Ile Met Arg Ser Asp Ala
        275                 280                 285
Pro Ile Gly Lys Cys Asn Ser Glu Cys Ile Thr Pro Asn Gly Ser Ile
    290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
        355                 360                 365
Phe Arg His Gln Asn Ser Glu Gly Ile Gly Gln Ala Ala Asp Leu Lys
    370                 375                 380
Ser Thr Gln Ala Ala Ile Asn Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
    450                 455                 460
Glu Arg Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
    530                 535                 540
Val Ala Leu Leu Gly Phe Ile Met Trp Ala Cys Gln Lys Gly Asn Ile
```

-continued

```
                545                 550                 555                 560

Arg Cys Asn Ile Cys Ile
                565

<210> SEQ ID NO 7
<211> LENGTH: 566
<212> TYPE: PRT
<213> ORGANISM: Influenza A virus

<400> SEQUENCE: 7

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Ala Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350
```

```
Gly Phe Ile Glu Asn Gly Trp Glu Gly Met Val Asp Gly Trp Tyr Gly
            355                 360                 365

Phe Arg His Gln Asn Ser Glu Gly Arg Gly Gln Ala Ala Asp Leu Lys
        370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 8
<211> LENGTH: 566
<212> TYPE: PRT
<213> ORGANISM: Influenza A virus

<400> SEQUENCE: 8

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160
```

```
Ser Ser Phe Phe Ser Arg Leu Asn Trp Leu Thr His Leu Asn Phe Lys
            165                 170                 175

Tyr Pro Ala Leu Asn Val Thr Met Pro Asn Asn Glu Gln Phe Asp Lys
        180                 185                 190

Leu Tyr Ile Trp Gly Val His His Pro Gly Thr Asp Lys Asp Gln Ile
    195                 200                 205

Phe Leu Tyr Ala Gln Ser Ser Gly Arg Ile Thr Val Ser Thr Lys Arg
210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
                565
```

<210> SEQ ID NO 9
<211> LENGTH: 566
<212> TYPE: PRT
<213> ORGANISM: Influenza A virus

<400> SEQUENCE: 9

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Ser Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380
```

```
Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
        420                 425                 430

Lys Ile Asp Leu Trp Ser Tyr Asn Ala Glu Leu Leu Val Ala Leu Glu
    435                 440                 445

Asn Gln His Thr Ile Asp Leu Thr Asp Ser Glu Met Asn Lys Leu Phe
450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
            485                 490                 495

Ile Arg Asn Gly Thr Tyr Asp His Asp Val Tyr Arg Asp Glu Ala Leu
        500                 505                 510

Asn Asn Arg Phe Gln Ile Lys Gly Val Glu Leu Lys Ser Gly Tyr Lys
    515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
            565

<210> SEQ ID NO 10
<211> LENGTH: 566
<212> TYPE: PRT
<213> ORGANISM: Influenza A virus

<400

```
                180                 185                 190
Leu Tyr Ile Trp Gly Val His His Pro Gly Thr Asp Lys Asp Gln Ile
            195                 200                 205

Phe Leu Tyr Ala Gln Ala Ser Gly Arg Ile Thr Val Ser Thr Lys Arg
        210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 11
<211> LENGTH: 566
<212> TYPE: PRT
<213> ORGANISM: Influenza A virus
```

```
<400> SEQUENCE: 11

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
```

-continued

```
                    405                 410                 415
Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
            485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Ala Leu Leu Gly Phe Ile Met Trp Ala Cys Gln Lys Gly Asn Ile
545                 550                 555                 560

Arg Cys Asn Ile Cys Ile
                565
```